(12) United States Patent
Thomas et al.

(10) Patent No.: US 11,684,749 B2
(45) Date of Patent: Jun. 27, 2023

(54) CATHETER WITH TAPERED SELF-INTRODUCING LOW-RECIRCULATION DISTAL TIP

(71) Applicant: Medical Components, Inc., Harleysville, PA (US)

(72) Inventors: Burton W. Thomas, Broomall, PA (US); Joshua L. Ballard, Asheville, NC (US); Jeffrey S. Bennett, Pottstown, PA (US); John M. Stephens, Perkiomenville, PA (US)

(73) Assignee: Medical Components, Inc., Harleysville, PA (US)

( * ) Notice: Subject to any disclaimer, the term of this patent is extended or adjusted under 35 U.S.C. 154(b) by 188 days.

(21) Appl. No.: 16/559,978

(22) Filed: Sep. 4, 2019

(65) Prior Publication Data

US 2021/0060292 A1 Mar. 4, 2021

(51) Int. Cl.
*A61M 25/00* (2006.01)

(52) U.S. Cl.
CPC ...... *A61M 25/0068* (2013.01); *A61M 25/003* (2013.01); *A61M 2025/0031* (2013.01); *A61M 2025/0035* (2013.01); *A61M 2025/0073* (2013.01)

(58) Field of Classification Search
CPC ...... A61M 25/0026; A61M 2025/0037; A61M 2025/0031; A61M 2025/0073
See application file for complete search history.

(56) References Cited

U.S. PATENT DOCUMENTS

| 8,092,415 B2 | 1/2012 | Moehle et al. |
| 8,894,601 B2 | 11/2014 | Moehle et al. |
| 9,579,485 B2 * | 2/2017 | Oborn ................. A61M 1/3661 |
| 2009/0187141 A1 | 7/2009 | Lareau et al. |
| 2014/0094741 A1 | 4/2014 | Bellisario et al. |
| 2014/0107591 A1 | 4/2014 | Hamatake et al. |

* cited by examiner

*Primary Examiner* — Laura A Bouchelle

(57) ABSTRACT

Disclosed is a multi-lumen catheter having a distal end catheter tip configured to improve fluid flow into and out from the catheter tip while reducing undesired recirculation during hemodialysis treatment of a patient. A first lumen and a second lumen each extends from the catheter proximal end to the catheter distal end, the first lumen and the second lumen being parallel to each other. A septum having a first side and a second side separates the first lumen from the second lumen. Some embodiments of the catheter tip include a beveled shape region, having a first lumen orifice, a second lumen orifice, and a septum top surface. Within the beveled shape region, at least a portion of the septum first side and at least a portion of the septum top surface form a first eave over the first lumen and at least a portion of the septum second side and at least a portion of the septum top surface form a second eave over the second lumen.

18 Claims, 13 Drawing Sheets

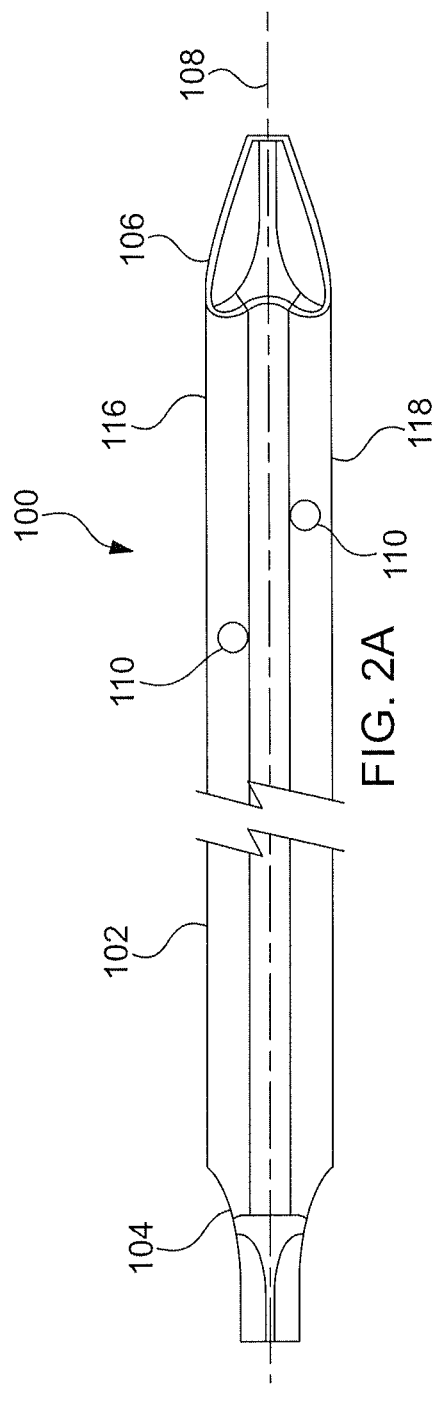
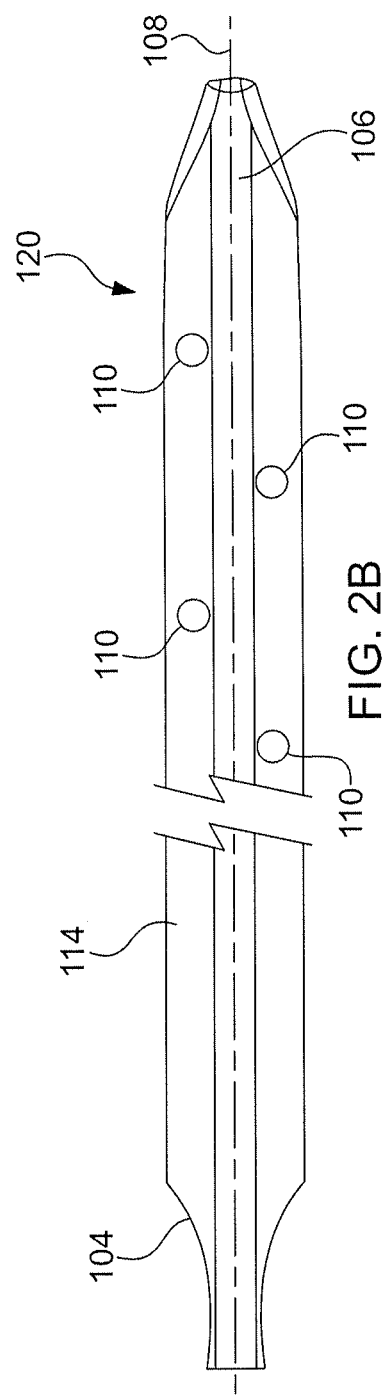
FIG. 2A
FIG. 2B

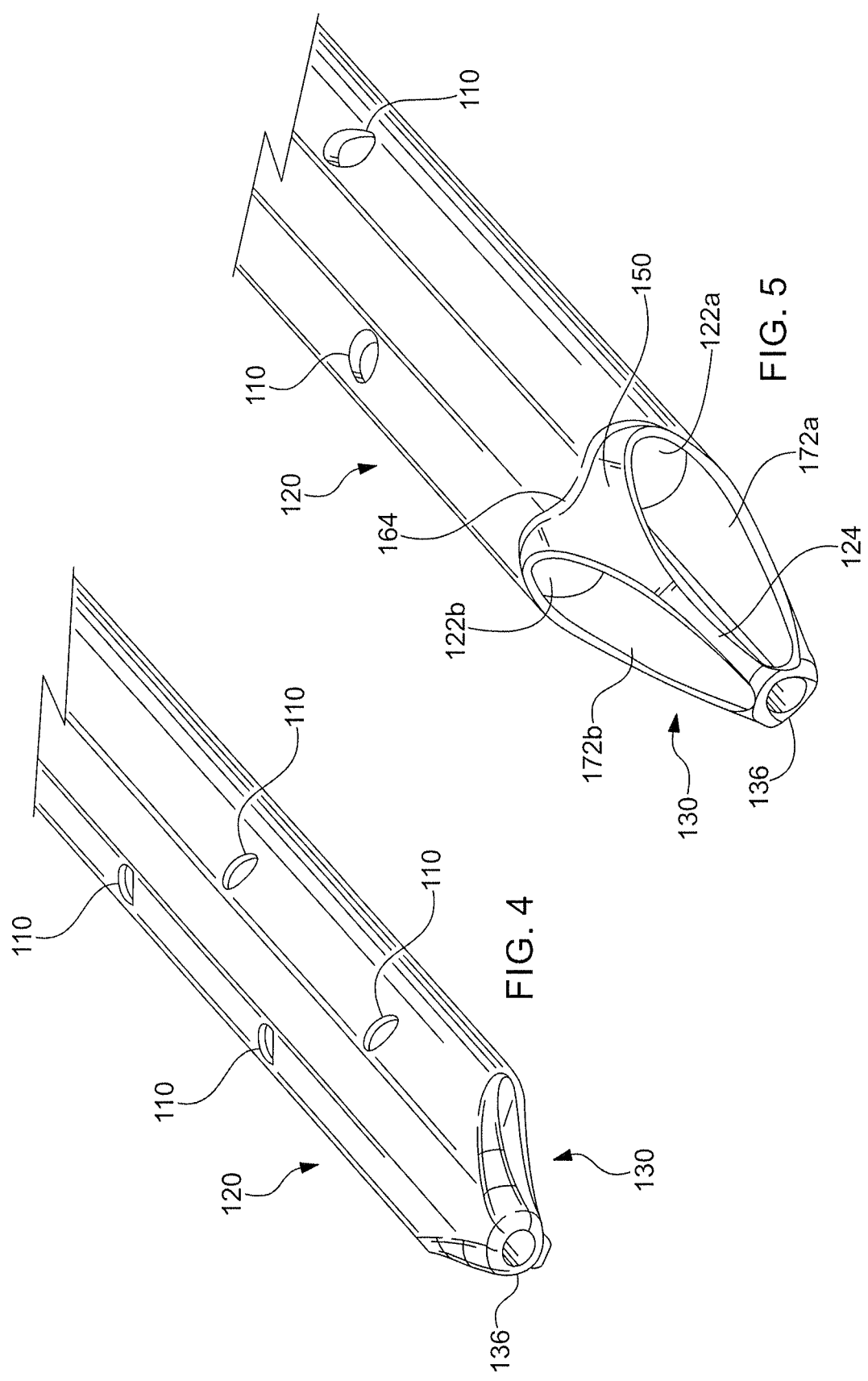

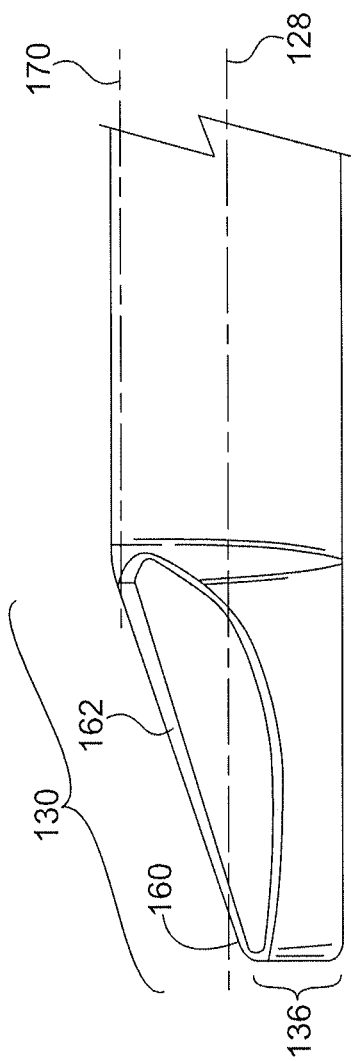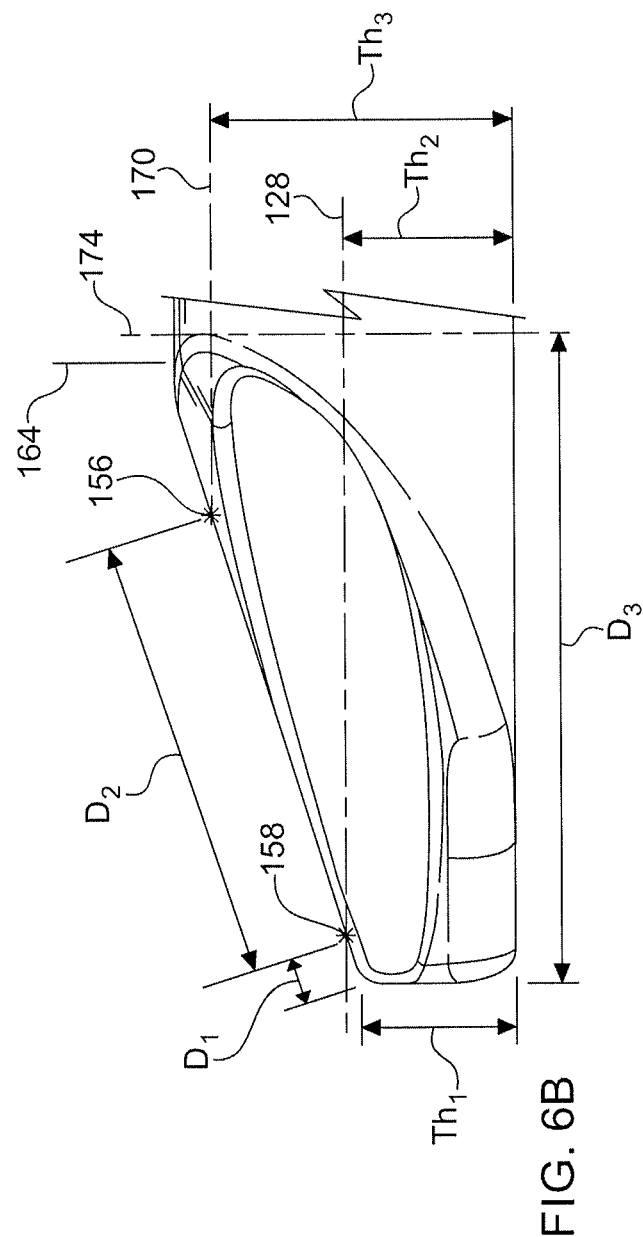

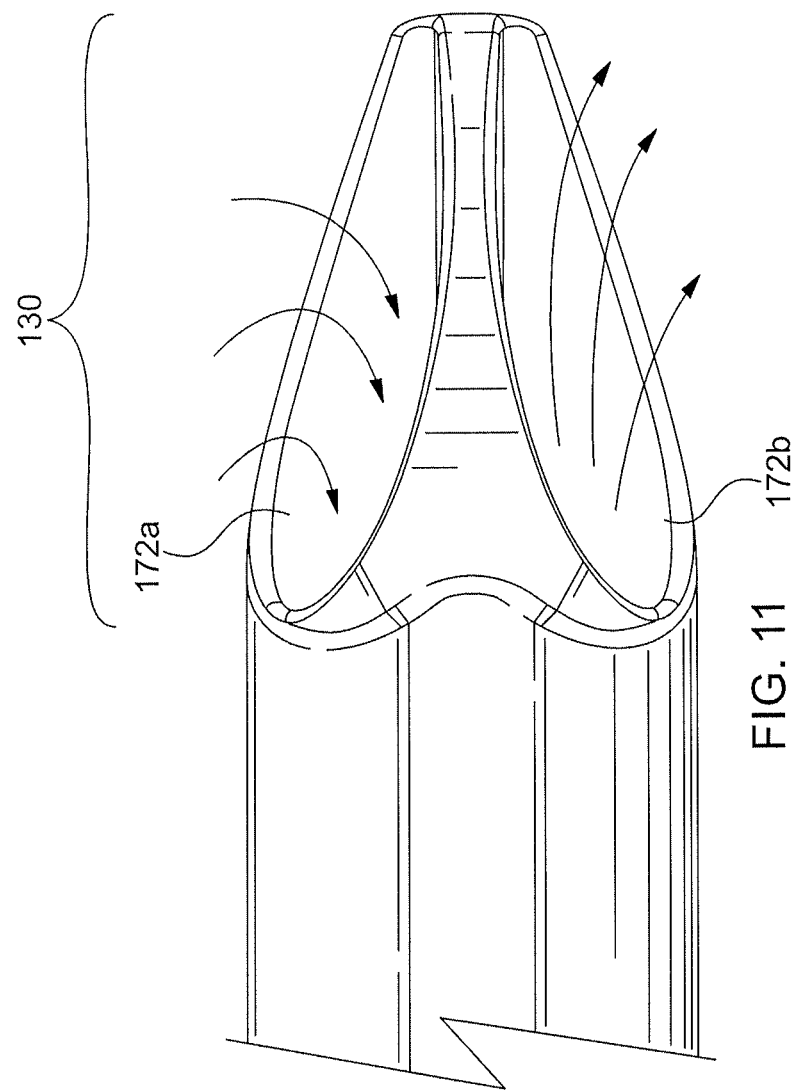

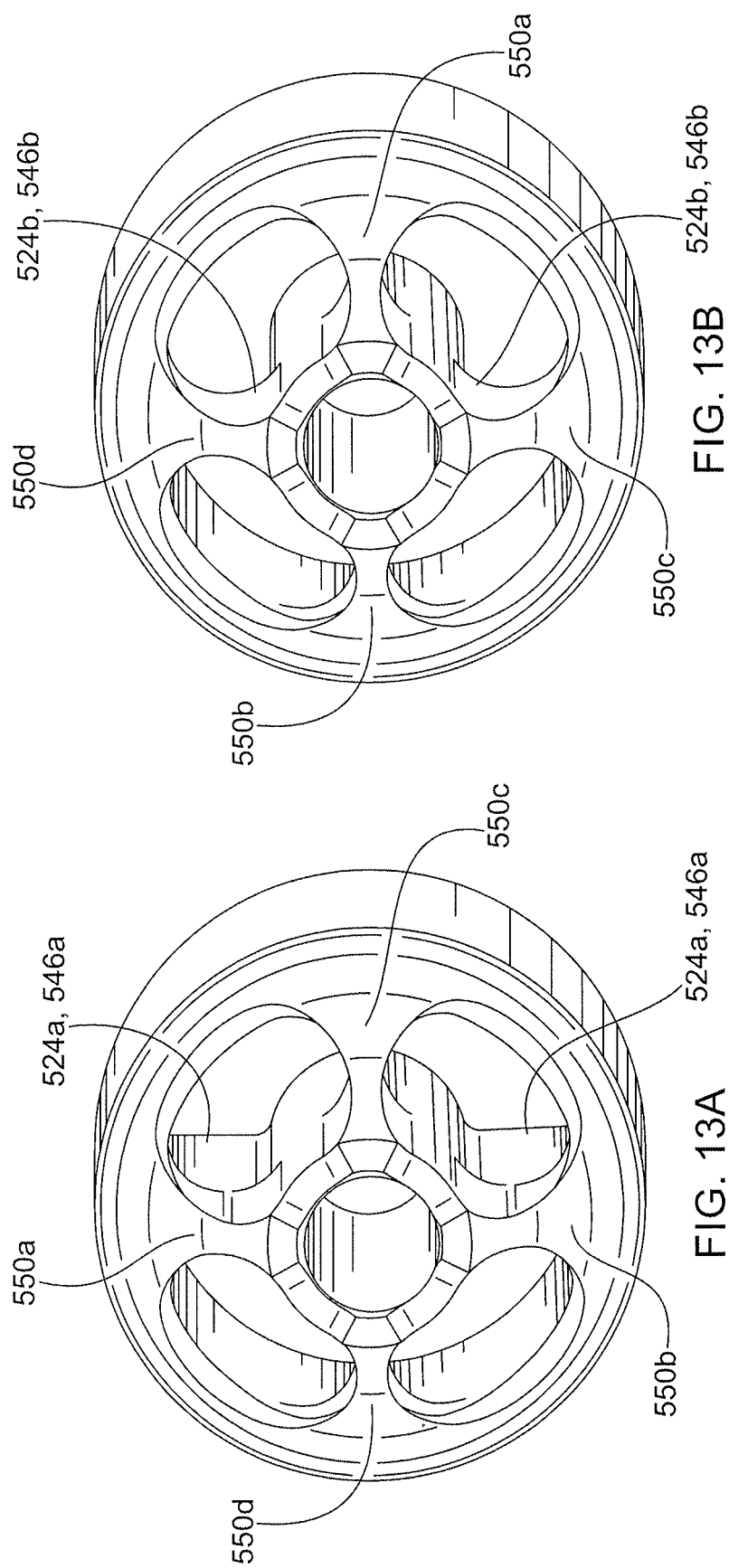

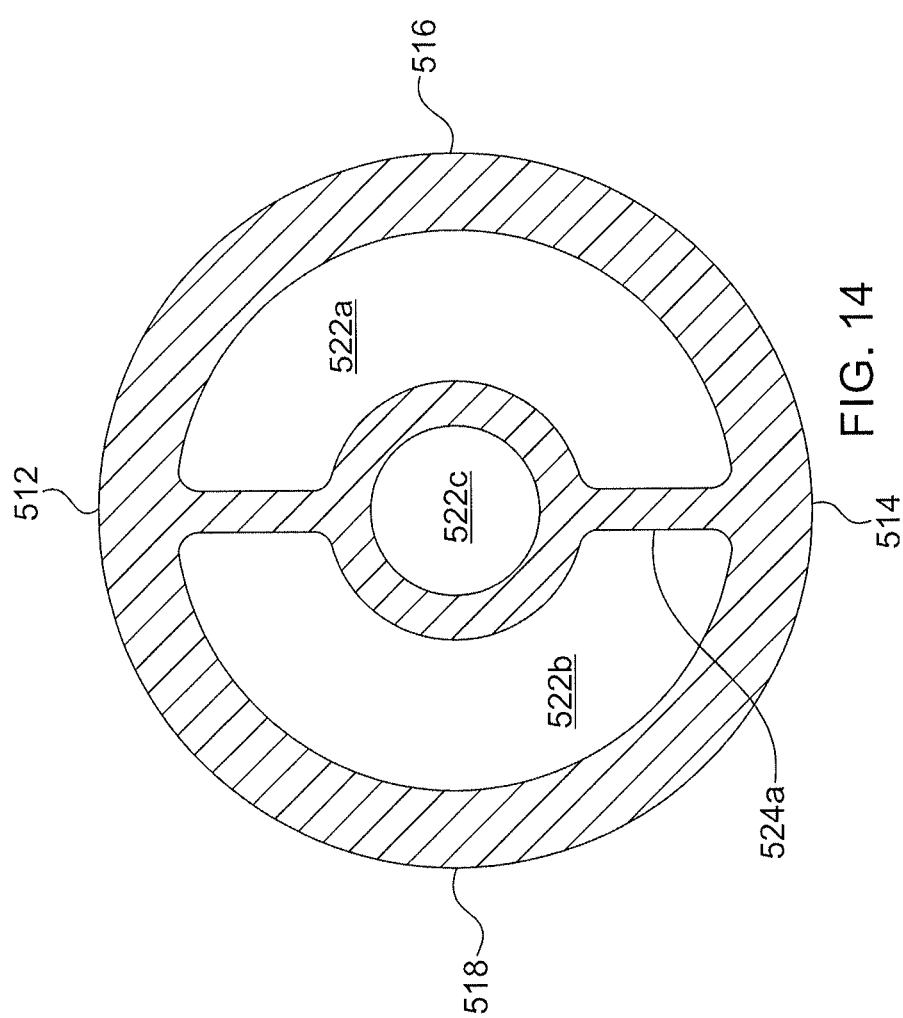

CATHETER WITH TAPERED SELF-INTRODUCING LOW-RECIRCULATION DISTAL TIP

FIELD OF THE INVENTION

The present disclosure relates to a catheter having a tip portion configured to improve fluid flow into and out from the tip portion, and to minimize undesired recirculation.

BACKGROUND OF THE INVENTION

Hemodialysis treatment typically includes removing toxic blood from the body, treating it with a dialyzer, and re-introducing it back into the body. Such treatment can further include access to a person's vascular system via a catheter. Generally, a catheter is inserted into a major vein and routed outside the patient to connectors permitting attachment of blood lines leading to and from the dialyzer. Catheters used for hemodialysis treatment can be configured as a dual-lumen catheter, wherein a first lumen can be a dedicated suction line and a second lumen can be a dedicated return line (or vice-versa). The suction line can be used to withdraw toxic blood from the body and the return line can be used to introduce treated blood to the body. In certain instances, such as one lumen of a catheter loses patency, the blood flow through the lumens can be reversed, i.e., the return line is now the suction line, and the suction line becomes the return line.

The effectiveness and efficiency of the catheter can depend on the amount and rate of toxic blood being withdrawn, the amount and rate of treated blood being introduced, and the amount and rate of treated blood being introduced via the return line that is undesirably withdrawn via the suction line. The treated blood being withdrawn via the suction line is generally referred to as undesired recirculation.

In certain applications, it is desirable that a hemodialysis catheter can be self-introducing, i.e., be able to be directly inserted into a patient's blood vessel. It is also desirable that the catheter tip and body have sufficient rigidity and also shaped to facilitate the self-introducing procedure.

Conventional catheter tip and multiple-lumen designs for reducing undesired recirculation can be limited in effectiveness and efficiency. Conventional designs can be appreciated from U.S. Pat. No. 8,092,415, U.S. Pat. Publ. No. 2009/0187141, U.S. Pat. Publ. No. 2014/0094741, and U.S. Pat. Publ. No. 2014/0107591.

SUMMARY OF THE INVENTION

Embodiments can include a catheter having a tip portion that is configured to improve fluid flow into and out from the tip portion, and to minimize undesired recirculation.

An embodiment of the catheter can include a catheter body having a catheter proximal end and a catheter distal end with a central longitudinal axis extending from the catheter proximal end to the catheter distal end. The catheter body can have a catheter top, a catheter bottom, a catheter first side, and a catheter second side. The catheter body can have a generally oval or stadium shaped cross-section. A geometric plane along the central longitudinal axis and extending from the catheter top to the catheter bottom can define a central longitudinal plane. A geometric plane along the central longitudinal axis, normal to the central longitudinal plane, and extending from the catheter first side to the catheter second side can define a central latitudinal plane.

The catheter body can have a height, $H_1$, defined along the central longitudinal plane and extending from the catheter top to the catheter bottom. In some embodiments, $H_1$ is within a range from 3.175 mm to 4.445 mm. The catheter body can have a width, $W_3$, defined along the central latitudinal plane and extending from the catheter first side to the catheter second side. In some embodiments, $W_3$ is within a range from 3.81 mm to 6.35 mm.

The catheter body can have a first lumen extending from the catheter proximal end to the catheter distal end, a second lumen extending from the catheter proximal end to the catheter distal end, the first lumen being adjacent the second lumen, the first lumen being separated from the second lumen by a septum. The septum can have a septum top surface at the distal end of the catheter.

The catheter distal end can have a catheter tip. The catheter tip can have a beveled shape region. The beveled shape region can have a bevel top edge at a proximal end of the beveled shape region and adjacent the catheter top. In some embodiments, the bevel top edge can be straight. In some embodiments, the bevel top edge can be curved.

The beveled shape region can have a chamfered edge at a distal end of the catheter tip. In some embodiments, the chamfered edge of the beveled shape region can have a thickness, $Th_1$. In some embodiments, $Th_1$ can be within a range from 0.5 mm to 2.5 mm.

The beveled shape region can have a first sidewall forming an outer portion of the first lumen and a second sidewall forming an outer portion of the second lumen. A first lateral plane tangential to the first sidewall and normal to the central latitudinal plane can be offset from the central longitudinal plane by an angle, $A_1$. A second lateral plane tangential to the second sidewall and normal to the central latitudinal plane can be offset from the central longitudinal plane by an angle, $A_2$. In some embodiments, angle $A_1$ can be within a range from 10 degrees to 30 degrees and angle $A_2$ can be within a range from 10 degrees to 30 degrees.

Within the beveled shape region, the first lumen can have a first lumen orifice having a first lumen orifice cross-section. The first lumen orifice cross-section can have a generally ovate shape, a generally oblong shape, or a generally tear-drop shape, etc. Within the beveled shape region, the second lumen can have a second lumen orifice having a second lumen orifice cross-section. The second lumen orifice cross-section can have a generally ovate shape, a generally oblong shape, or a generally tear-drop shape, etc. In some embodiments, the first lumen orifice cross-section can have a generally ovate shape with a first major axis and a first minor axis and the second lumen orifice cross-section can have a generally ovate shape with a second major axis and a second minor axis.

In some embodiments, the length of the first major axis is equal to the length of the second major axis. In some embodiments, the length of the first minor axis is equal to the length of the second minor axis. In some embodiments, a ratio of a first major axis to a first minor axis can be within a range from 3 to 5. In some embodiments, the first major axis can be within a range from 5 mm to 10 mm, and the first minor axis can be within a range from 0.5 mm to 3.0 mm. In some embodiments, a ratio of a second major axis to a second minor axis can be within a range from 3 to 5. In some embodiments, the second major axis can be within a range from 5 mm to 10 mm, and the second minor axis can be within a range from 0.5 mm to 3 mm.

In some embodiments, the first major axis is not an axis of symmetry. In some embodiments, the second major axis is not an axis of symmetry. In some embodiments, the first minor axis is not an axis of symmetry. In some embodiments, the second minor axis is not an axis of symmetry.

In some embodiments, the septum can have a septum first side forming part of the first lumen and a septum second side forming part of the second lumen. The septum within the beveled shape region can have a septum top surface. The septum top surface can form a first eave over the first lumen comprising at least a portion of the septum first side and at least a portion of the septum top surface. The septum top surface can form a second eave over the second lumen comprising the at least a portion of the septum second side and at least a portion of the septum top surface. For example, the first eave formed over the first lumen can include a region of the septum first side within the beveled shape region leading up into the septum top surface and the half of the septum top surface spanning from the central longitudinal plane to the first lumen orifice. The second eave formed over the second lumen can include a region of the septum second side within the beveled shape region leading up into the septum top surface and the half of the septum top surface spanning from the central longitudinal plane to the second lumen orifice. It is contemplated that the first eave can have a curved or arched shape that forms at least a portion of the first lumen orifice and the second eave can have a curved or arched shape that forms at least a portion of the second lumen orifice. In some embodiments, the first eave acts as a baffle to direct fluid flow out from the first lumen via the first lumen orifice, while restricting cross-over fluid flow to the second lumen, thereby reducing undesired recirculation. In some embodiments, the second eave acts as a baffle to direct fluid flow out from the second lumen via the second lumen orifice, while restricting cross-over fluid flow to the first lumen, thereby reducing undesired recirculation. It is contemplated that the first lumen and the second lumen are configured to be interchangeable. For example, the first lumen can be a dedicated suction line and the second lumen can be a dedicated return line (or vice-versa). The suction line can be used to withdraw toxic blood from the body and the return line can be used to introduce treated blood to the body.

A geometric plane parallel to the central latitudinal plane and bisecting the septum top surface at the top of the first lumen orifice and at the top of the second lumen orifice can define an upper latitudinal plane. It is contemplated that the septum top surface can be bisected by the central latitudinal plane at a central latitudinal axis and that the septum top surface can be bisected by the upper latitudinal plane at an upper latitudinal axis. In some embodiments, the septum can have a septum first segment that extends along the septum top surface from the catheter distal end for a distance $D_1$ to the central latitudinal axis. In some embodiments, the septum can have a septum second segment that extends along the septum top surface from the central latitudinal axis for a distance $D_2$ to the upper latitudinal axis. The septum top surface at the central latitudinal axis can have a width $W_1$. The septum second segment gradually widens as the septum extends from the central latitudinal plane to the upper latitudinal plane. The septum top surface at the upper latitudinal axis can have a width $W_2$.

In some embodiments, the distance $D_1$ can be within a range from 0.25 mm to 0.75 mm. In some embodiments, the distance $D_2$ can be within a range from 2.5 mm to 7.5 mm.

In some embodiments, the septum top surface at the central latitudinal axis can have a width $W_1$ and the septum top surface at the upper latitudinal axis can have a width $W_2$, wherein $W_1$ is less than $W_2$. In some embodiments, $W_1$ can be within a range from 0.25 mm to 1.5 mm. In some embodiments, $W_2$ can be within a range from 1.5 mm to 3.5 mm.

In some embodiments, a geometric axis perpendicular to the central latitudinal plane, extending from the catheter top to the catheter bottom, and tangential to the bevel top edge defines a z-axis. The beveled shape region can extend for a distance, $D_3$, measured parallel to the central latitudinal plane, from the chamfered edge at the catheter distal end to the z-axis. In some embodiments, $D_3$ can be within a range from 6.35 mm to 7.62 mm.

In some embodiments, the catheter body can have a thickness, $Th_2$, along the central longitudinal plane and extending from the catheter bottom to the central latitudinal plane. In some embodiments, $Th_2$ can be within a range from 0.55 mm to 3.4 mm.

In some embodiments, the catheter body can have a thickness, $Th_3$, along the central longitudinal plane and extending from the catheter bottom to the upper latitudinal plane. In some embodiments, $Th_3$ can be within a range from 1.0 mm to 8.7 mm.

In some embodiments, $Th_1$ is less than $Th_2$ and $Th_2$ is less than $Th_3$.

In some embodiments, the catheter can have a third lumen extending from the catheter proximal end to the catheter distal end and having a third lumen orifice at the catheter distal end. The third lumen can be positioned adjacent the first lumen and adjacent the second lumen. In some embodiments, the third lumen can have a generally circular shaped cross-section. In some embodiments, the third lumen can be positioned adjacent the catheter bottom.

Some embodiments can include at least one aperture formed in the catheter top that extends into at least one of the first lumen and the second lumen. Some embodiments can include a first aperture formed in the catheter top that extends into the first lumen, and a second aperture formed into the catheter top that extends into the second lumen. Some embodiments can include at least one aperture formed in the catheter bottom that extends into at least one of the first lumen and the second lumen. Some embodiments can include: a first aperture formed in the catheter bottom that extends into the first lumen; a second aperture formed in the catheter bottom that extends into the first lumen; a third aperture formed in the catheter bottom that extends into the second lumen; and a fourth aperture formed into the catheter bottom that extends into the second lumen.

Alternative embodiments of the catheter can include a catheter body having a catheter proximal end and a catheter distal end with a central longitudinal axis extending from the catheter proximal end to the catheter distal end. The catheter body can have a catheter top, a catheter bottom, a catheter first side, and a catheter second side. The catheter body can have a generally circular shaped cross-section. A geometric plane along the central longitudinal axis and extending from the catheter top to the catheter bottom can define a central longitudinal plane. A geometric plane along the central longitudinal axis, normal to the central longitudinal plane, and extending from the catheter first side to the catheter second side can define a central latitudinal plane.

The catheter body can have a first lumen extending from the catheter proximal end to the catheter distal end, a second lumen extending from the catheter proximal end to the catheter distal end, the first lumen being adjacent the second lumen, the first lumen being separated from the second lumen by a first septum. The first septum can extend along the central longitudinal plane from the catheter proximal end to the catheter distal end.

The catheter distal end can have a catheter tip. In some embodiments, the catheter tip can have a conical shaped region. The conical shaped region can have a conical frustum shape having a flat distal edge at a distal end of the catheter tip. The flat distal edge of the conical shaped region can have a thickness, $Th_4$.

In some embodiments, the conical shaped region can have a second septum, normal to the first septum, the second septum extending from a proximal end of the conical shaped region to a distal end of the conical shaped region. The second septum can bisect the first lumen within the conical shaped region and can bisect the second lumen within the conical shaped region. In some embodiments, within the conical shaped region, the first lumen can have a first lumen upper orifice and a first lumen lower orifice, the first lumen upper orifice and the first lumen lower orifice being separated by the second septum. In some embodiments, within the conical shaped region, the second lumen can have a second lumen upper orifice and a second lumen lower orifice, the second lumen upper orifice and the second lumen lower orifice being separated by the second septum.

In some embodiments, the first septum separating the first lumen from the second lumen can have a septum top surface within the conical shaped region, the septum top surface separating the first lumen upper orifice from the second lumen upper orifice. The first septum can have a septum bottom surface within the conical shaped region, the septum bottom surface separating the first lumen lower orifice from the second lumen lower orifice. The second septum can have a septum first lateral surface within the conical shaped region, the septum first lateral surface separating the first lumen upper orifice from the first lumen lower orifice. The second septum can have a septum second lateral surface within the conical shaped region, the septum second lateral surface separating the second lumen upper orifice from the second lumen lower orifice.

Within the conical shaped region, the first lumen upper orifice can have a first lumen upper orifice cross-section and the first lumen lower orifice can have a first lumen lower orifice cross-section. Each of the first lumen upper orifice cross-section and the first lumen lower orifice cross-section can have a generally ovate shape, a generally oblong shape, or a generally tear-drop shape, etc. Within the conical shaped region, the second lumen upper orifice can have a second lumen upper orifice cross-section and the second lumen lower orifice can have a second lumen lower orifice cross-section. Each of the second lumen upper orifice cross-section and the second lumen lower orifice cross-section can have a generally ovate shape, a generally oblong shape, or a generally tear-drop shape, etc.

In some embodiments, the first lumen upper orifice cross-section can have a generally ovate shape with a first upper major axis and a first upper minor axis, the first lumen lower orifice cross-section can have a generally ovate shape with a first lower major axis and a first lower minor axis, the second lumen upper orifice cross-section can have a generally ovate shape with a second upper major axis and a second upper minor axis, and the second lumen lower orifice cross-section can have a generally ovate shape with a second lower major axis and a second lower minor axis. In some embodiments, each of the first upper major axis, the first lower major axis, the second upper major axis, and the second lower major axis is an axis of symmetry. In some embodiments, each of the first upper major axis, the first lower major axis, the second upper major axis, and the second lower major axis is not an axis of symmetry. In some embodiments, each of the first upper minor axis, the first lower minor axis, the second upper minor axis, and the second lower minor axis is not an axis of symmetry.

In some embodiments, the conical shaped region can have a plurality of eaves formed adjacent the first lumen upper orifice, adjacent the first lumen lower orifice, adjacent the second lumen upper orifice, and adjacent the second lumen lower orifice. For example, the first septum can have a first septum first side forming part of the first lumen and a first septum second side forming part of the second lumen. The first eave formed over the first lumen can include a region of the first septum first side leading up into the septum top surface and the half of the septum top surface spanning from the central longitudinal plane to the first lumen upper orifice. The second eave formed over the second lumen can include a region of the first septum second side leading up into the septum top surface and the half of the septum top surface spanning from the central longitudinal plane to the second lumen upper orifice. The third eave formed over the first lumen can include a region of the first septum first side leading up into the septum bottom surface and the half of the septum bottom surface spanning from the central longitudinal plane to the first lumen lower orifice. The fourth eave formed over the second lumen can include a region of the first septum second side leading up into the septum bottom surface and the half of the septum bottom surface spanning from the central longitudinal plane to the second lumen lower orifice.

It is contemplated that the first eave can have a curved or arched shape that forms at least a portion of the first lumen upper orifice, the second eave can have a curved or arched shape that forms at least a portion of the second lumen upper orifice, the third eave can have a curved or arched shape that forms at least a portion of the first lumen lower orifice, and the fourth eave can have a curved or arched shape that forms at least a portion of the second lumen lower orifice.

In some embodiments, the conical shaped region can have a plurality of eaves formed adjacent the first lumen upper orifice, adjacent the first lumen lower orifice, adjacent the second lumen upper orifice, and adjacent the second lumen lower orifice. For example, the second septum can have a second septum first side and a second septum second side. The fifth eave formed over the first lumen can include a region of the second septum first side leading up into the septum first lateral surface and the half of the septum first lateral surface spanning from the central latitudinal plane to the first lumen upper orifice. The sixth eave formed over the first lumen can include a region of the second septum second side leading up into the septum first lateral surface and the half of the septum first lateral surface spanning from the central latitudinal plane to the first lumen lower orifice. The seventh eave formed over the second lumen can include a region of the second septum first side leading up into the septum second lateral surface and the half of the septum second lateral surface spanning from the central latitudinal plane to the second lumen upper orifice. The eighth eave formed over the second lumen can include a region of the second septum second side leading up into the septum second lateral surface and the half of the septum second lateral surface spanning from the central latitudinal plane to the second lumen lower orifice.

It is contemplated that the fifth eave can have a curved or arched shape that forms at least a portion of the first lumen upper orifice, the sixth eave can have a curved or arched shape that forms at least a portion of the first lumen lower orifice, the seventh eave can have a curved or arched shape that forms at least a portion of the second lumen upper orifice, and the eighth eave can have a curved or arched shape that forms at least a portion of the second lumen lower orifice.

In some embodiments, each of the first eave and the fifth eave acts as a baffle to direct fluid flow out from the first lumen via the first lumen upper orifice, while restricting cross-over fluid flow to the second lumen, thereby reducing undesired recirculation. In some embodiments, each of the third eave and the sixth eave act as a baffle to direct fluid flow out from the first lumen via the first lumen lower orifice, while restricting cross-over fluid flow to the second lumen, thereby reducing undesired recirculation. In some embodiments, each of the second eave and the seventh eave acts as a baffle to direct fluid flow out from the second lumen via the second lumen upper orifice, while restricting cross-over fluid flow to the first lumen, thereby reducing undesired recirculation. In some embodiments, each of the fourth eave and the eighth eave acts as a baffle to direct fluid flow out from the second lumen via the second lumen lower orifice, while restricting cross-over fluid flow to the first lumen, thereby reducing undesired recirculation.

It is contemplated that the first lumen and the second lumen are configured to be interchangeable. For example, the first lumen can be a dedicated suction line and the second lumen can be a dedicated return line (or vice-versa). The suction line can be used to withdraw toxic blood from the body and the return line can be used to introduce treated blood to the body.

In some embodiments, the catheter can have a third lumen extending from the catheter proximal end to the catheter distal end and having a third lumen orifice at the catheter distal end. The third lumen can be positioned adjacent the first lumen and adjacent the second lumen. In some embodiments, the third lumen can have a generally circular shaped cross-section. In some embodiments, the third lumen can be positioned centrally within the catheter body such that the third lumen bisects the first septum and bisects the second septum.

Some embodiments can include at least one aperture formed in the catheter top that extends into at least one of the first lumen and the second lumen. Some embodiments can include a first aperture formed in the catheter top that extends into the first lumen, and a second aperture formed into the catheter top that extends into the second lumen. Some embodiments can include at least one aperture formed in the catheter bottom that extends into at least one of the first lumen and the second lumen. Some embodiments can include: a first aperture formed in the catheter bottom that extends into the first lumen; a second aperture formed in the catheter bottom that extends into the first lumen; a third aperture formed in the catheter bottom that extends into the second lumen; and a fourth aperture formed into the catheter bottom that extends into the second lumen.

The present disclosure generally relates to a multi-lumen catheter, which may comprise an elongated catheter body comprising a catheter top, a catheter bottom, a catheter first side, and a catheter second side; a proximal end; a distal end having a catheter tip; a first lumen extending from the catheter proximal end to the catheter distal end and a second lumen extending from the catheter proximal end to the catheter distal end, wherein the first lumen is substantially parallel to the second lumen; a septum comprising a septum first side adjacent the first lumen and a septum second side adjacent the second lumen, wherein the septum separates the first lumen from the second lumen; and a beveled shape region comprising a first lumen orifice, a second lumen orifice, at least a portion of the septum first side, at least a portion of the septum second side, and a septum top surface; wherein at least a portion of the septum first side and at least a portion of the septum top surface form a first eave over the first lumen; and at least a portion of the septum second side and at least a portion of the septum top surface form a second eave over the second lumen.

In some embodiments, the multi-lumen catheter may further comprise a central longitudinal axis extending from the catheter proximal end to the catheter distal end; a central longitudinal plane comprising the central longitudinal axis and extending from the catheter top to the catheter bottom; a central latitudinal plane comprising the central longitudinal axis and extending from the catheter first side to the catheter second side; an upper latitudinal plane parallel to the central latitudinal plane and bisecting the septum top surface at the top of the first lumen orifice and at the top of the second lumen orifice; a central latitudinal axis extending along the central latitudinal plane and bisecting the septum top surface; and an upper latitudinal axis extending along the upper latitudinal plane and bisecting the septum top surface.

In some embodiments, the first eave may comprise a region of the septum first side leading up into the septum top surface and a half of the septum top surface spanning from the central longitudinal plane to the first lumen orifice; the second eave may comprise a region of the septum second side leading up into the septum top surface and a half of the septum top surface spanning from the central longitudinal plane to the second lumen orifice; the first eave having a curved or arched shape that forms at least a portion of the first lumen orifice and the second eave having a curved or arched shape that forms at least a portion of the second lumen orifice.

In some embodiments, the first eave may be configured to act as a baffle to direct fluid flow out from the first lumen via the first lumen orifice, while restricting cross-over fluid flow to the second lumen, thereby reducing undesired recirculation; and the second eave may be configured to act as a baffle to direct fluid flow out from the second lumen via the second lumen orifice, while restricting cross-over fluid flow to the first lumen, thereby reducing undesired recirculation.

In some embodiments, the first lumen can be a dedicated suction line or a dedicated return line; and the second lumen can be a dedicated suction line or a dedicated return line.

In some embodiments, the catheter body may comprise a generally oval or stadium shaped cross-section; a height, $H_1$, measured along the central longitudinal axis and extending from the catheter bottom to the catheter top; and a width, $W_3$, measured along the central latitudinal axis and extending from the catheter first side to the catheter second side; wherein $H_1$ is less than $W_3$.

In some embodiments, $H_1$ can be within a range from 3.175 mm to 4.445 mm; and $W_3$ can be within a range from 3.81 mm to 6.35 mm.

In some embodiments, the septum may comprise a width, $W_1$, measured along the central latitudinal axis and extending from the septum first side to the septum second side; and a width, $W_2$, measured along the upper latitudinal axis and extending from the septum first side to the septum second side, wherein $W_1$ is less than $W_2$.

In some embodiments, $W_1$ can be within a range from 0.25 mm to 1.5 mm; and $W_2$ can be within a range from 1.5 mm to 3.5 mm.

In some embodiments, the beveled shape region may comprise a chamfered edge at the distal end of the catheter.

In some embodiments, the chamfered edge may have a thickness, $Th_1$, measured along the central longitudinal plane.

In some embodiments, $Th_1$ can be within a range from 0.5 mm to 2.5 mm.

In some embodiments, the beveled shape region may comprise a bevel top edge at a proximal end of the beveled shape region and adjacent the catheter top, wherein the bevel top edge can be straight or curved.

In some embodiments, the septum may comprise a septum first segment extending along the septum top surface from the catheter distal end for a distance, $D_1$, to the central latitudinal axis; and a septum second segment extending along the septum top surface from the central latitudinal axis for a distance, $D_2$, to the upper latitudinal axis.

In some embodiments, $D_1$ can be within a range from 0.25 mm to 0.75 mm; and $D_2$ can be within a range from 2.5 mm to 7.5 mm.

In some embodiments, the beveled shape region may extend for a distance, $D_3$, measured parallel to the central latitudinal plane, from the chamfered edge at the catheter distal end to a z-axis; wherein the z-axis is perpendicular to the central latitudinal plane, tangential to the bevel top edge, and extends from the catheter top to the catheter bottom.

In some embodiments, $D_3$ can be within a range from 6.35 mm to 7.62 mm.

In some embodiments, the catheter body may have a thickness, $Th_2$, and a thickness $Th_3$, wherein $Th_2$ is measured along the central longitudinal plane and extends from the catheter bottom to the central latitudinal plane; and $Th_3$ is measured along the central longitudinal plane and extends from the catheter bottom to the upper latitudinal plane.

In some embodiments, $Th_2$ can be within a range from 0.55 mm to 3.4 mm; and $Th_3$ can be within a range from 1.0 mm to 8.7 mm.

In some embodiments, the catheter body may comprise at least one aperture.

In some embodiments, the catheter body may comprise at least one aperture extending through the catheter top and into at least one of the first lumen and the second lumen.

In some embodiments, the catheter body may comprise at least one aperture extending through the catheter bottom and into at least one of the first lumen and the second lumen.

In some embodiments, the multi-lumen catheter may further comprise a third lumen adjacent the first lumen and adjacent the second lumen.

In some embodiments, the beveled shape region may comprise a first sidewall forming an outer portion of the first lumen; and a second sidewall forming an outer portion of the second lumen; wherein a first lateral plane tangential to the first sidewall and normal to the central latitudinal plane is offset from the central longitudinal plane by an angle, $A_1$; and a second lateral plane tangential to the second sidewall and normal to the central latitudinal plane is offset from the central longitudinal plane by an angle, $A_2$.

In some embodiments, angle $A_1$ can be within a range from 10 degrees to 30 degrees; and angle $A_2$ can be within a range from 10 degrees to 30 degrees.

In some embodiments, the beveled shape region may comprise a first lumen orifice cross-section of the first lumen orifice, wherein the first lumen orifice cross-section can have a generally ovate shape, a generally oblong shape, or a generally tear-drop shape; and a second lumen orifice cross-section of the second lumen orifice, wherein the second lumen orifice cross-section can have a generally ovate shape, a generally oblong shape, or a generally tear-drop shape.

In some embodiments, the first lumen orifice cross-section may have a generally ovate shape with a first major axis and a first minor axis, and the second lumen orifice cross-section may have a generally ovate shape with a second major axis and a second minor axis.

In some embodiments, each of the first major axis and the second major axis can be within a range from 5.0 mm to 10.0 mm; and each of the first minor axis and the second minor axis can be within a range from 0.5 mm to 3 mm.

In some embodiments, a ratio of the first major axis to the first minor axis can be within a range from 3 to 5 and a ratio of the second major axis to the second minor axis can be within a range from 3 to 5.

In some embodiments, the beveled shape region may comprise at least one plane of symmetry, wherein the plane of symmetry is the central longitudinal plane.

In some embodiments, the multi-lumen catheter may be configured to improve fluid flow into and out from the catheter tip and to reduce undesired recirculation during hemodialysis treatment of a patient.

The present disclosure generally relates to a multi-lumen catheter, which may comprise an elongated catheter body comprising a catheter top, a catheter bottom, a catheter first side, and a catheter second side; a proximal end; a distal end having a catheter tip; a first lumen extending from the catheter proximal end to the catheter distal end and a second lumen extending from the catheter proximal end to the catheter distal end, wherein the first lumen is substantially parallel to the second lumen; a first septum comprising a first septum first side adjacent the first lumen and a first septum second side adjacent the second lumen, wherein the first septum separates the first lumen from the second lumen; and a conical shaped region. The conical shaped region may comprise a first lumen upper orifice, a first lumen lower orifice, and second lumen upper orifice, and a second lumen lower orifice. The conical shaped region may further comprise a second septum having a second septum first side and a second septum second side; wherein the second septum is normal to the first septum; wherein the second septum separates the first lumen upper orifice from the first lumen lower orifice; and wherein the second septum separates the second lumen upper orifice from the second lumen lower orifice. The conical shaped region may further comprise at least a portion of the first septum first side and at least a portion of the first septum second side, a septum top surface, a septum bottom surface, a septum first lateral surface, and a septum second lateral surface; wherein at least a portion of the first septum first side and at least a portion of the septum top surface form a first eave over the first lumen; wherein at least a portion of the first septum second side and at least a portion of the septum top surface form a second eave over the second lumen; wherein at least a portion of the first septum first side and at least a portion of the septum bottom surface form a third eave over the first lumen; wherein at least a portion of the first septum second side and at least a portion of the septum bottom surface form a fourth eave over the second lumen; wherein at least a portion of the second septum first side and at least a portion of the septum first lateral surface form a fifth eave over the first lumen; wherein at least a portion of the second septum second side and at least a portion of the septum first lateral surface form a sixth eave over the first lumen; wherein at least a portion of the second septum first side and at least a portion of the septum second lateral surface form a seventh eave over the second lumen; and wherein at least a portion of the second septum second side and at least a portion of the septum second lateral surface form an eighth eave over the second lumen.

In some embodiments, the multi-lumen catheter may further comprise a central longitudinal axis extending from the catheter proximal end to the catheter distal end; a central longitudinal plane comprising the central longitudinal axis and extending from the catheter top to the catheter bottom; and a central latitudinal plane comprising the central longitudinal axis and extending from the catheter first side to the catheter second side.

In some embodiments, the first eave may comprise a region of the first septum first side leading up into the septum top surface and a half of the septum top surface spanning from the central longitudinal plane to the first lumen upper orifice, the first eave having a curved or arched shape that forms at least a portion of the first lumen upper orifice; the second eave may comprise a region of the first septum second side leading up into the septum top surface and a half of the septum top surface spanning from the central longitudinal plane to the second lumen upper orifice, the second eave having a curved or arched shape that forms at least a portion of the second lumen upper orifice; the third eave may comprise a region of the first septum first side leading up into the septum bottom surface and a half of the septum bottom surface spanning from the central longitudinal plane to the first lumen lower orifice, the third eave having a curved or arched shape that forms at least a portion of the first lumen lower orifice; the fourth eave may comprise a region of the first septum second side leading up into the septum bottom surface and a half of the septum bottom surface spanning from the central longitudinal plane to the second lumen lower orifice, the fourth eave having a curved or arched shape that forms at least a portion of the second lumen lower orifice; the fifth eave may comprise a region of the second septum first side leading up into the septum first lateral surface and a half of the septum first lateral surface spanning from the central latitudinal plane to the first lumen upper orifice, the fifth eave having a curved or arched shape that forms at least a portion of the first lumen upper orifice; the sixth eave may comprise a region of the second septum second side leading up into the septum first lateral surface and a half of the septum first lateral surface spanning from the central latitudinal plane to the first lumen lower orifice, the sixth eave having a curved or arched shape that forms at least a portion of the first lumen lower orifice; the seventh eave may comprise a region of the second septum first side leading up into the septum second lateral surface and a half of the septum second lateral surface spanning from the central latitudinal plane to the second lumen upper orifice, the seventh eave having a curved or arched shape that forms at least a portion of the second lumen upper orifice; and the eighth eave may comprise a region of the second septum second side leading up into the septum second lateral surface and a half of the septum second lateral surface spanning from the central latitudinal plane to the second lumen lower orifice, the eighth eave having a curved or arched shape that forms at least a portion of the second lumen lower orifice.

In some embodiments, the first eave may be configured to act as a baffle to direct fluid flow out from the first lumen via the first lumen upper orifice, while restricting cross-over fluid flow to the second lumen, thereby reducing undesired recirculation; the second eave may be configured to act as a baffle to direct fluid flow out from the second lumen via the second lumen upper orifice, while restricting cross-over fluid flow to the first lumen, thereby reducing undesired recirculation; the third eave may be configured to act as a baffle to direct fluid flow out from the first lumen via the first lumen lower orifice, while restricting cross-over fluid flow to the second lumen, thereby reducing undesired recirculation; the fourth eave may be configured to act as a baffle to direct fluid flow out from the second lumen via the second lumen lower orifice, while restricting cross-over fluid flow to the first lumen, thereby reducing undesired recirculation; the fifth eave may be configured to act as a baffle to direct fluid flow out from the first lumen via the first lumen upper orifice, while restricting cross-over fluid flow to the second lumen, thereby reducing undesired recirculation; the sixth eave may be configured to act as a baffle to direct fluid flow out from the first lumen via the first lumen lower orifice, while restricting cross-over fluid flow to the second lumen, thereby reducing undesired recirculation; the seventh eave may be configured to act as a baffle to direct fluid flow out from the second lumen via the second lumen upper orifice, while restricting cross-over fluid flow to the first lumen, thereby reducing undesired recirculation; and the eighth eave may be configured to act as a baffle to direct fluid flow out from the second lumen via the second lumen lower orifice, while restricting cross-over fluid flow to the first lumen, thereby reducing undesired recirculation.

In some embodiments, the first lumen can be a dedicated suction line or a dedicated return line; and the second lumen can be a dedicated suction line or a dedicated return line.

In some embodiments, the catheter body may comprise a generally circular shaped cross-section.

In some embodiments, the conical shaped region may comprise a flat distal edge at the distal end of the catheter.

In some embodiments, the flat distal edge may have a thickness, $Th_4$, measured along the central longitudinal plane.

In some embodiments, the catheter body may comprise at least one aperture.

In some embodiments, the catheter body may comprise at least one aperture extending through the catheter top and into at least one of the first lumen and the second lumen.

In some embodiments, the catheter body may comprise at least one aperture extending through the catheter bottom and into at least one of the first lumen and the second lumen.

In some embodiments, the multi-lumen catheter may further comprise a third lumen adjacent the first lumen and adjacent the second lumen.

In some embodiments, the third lumen may have a generally circular shaped cross-section.

In some embodiments, the third lumen may be positioned centrally within the catheter body such that the third lumen bisects the first septum and bisects the second septum.

In some embodiments, the conical shaped region may comprise a first lumen upper orifice cross-section of the first lumen upper orifice, wherein the first lumen upper orifice cross-section can have a generally ovate shape, a generally oblong shape, or a generally tear-drop shape; a first lumen lower orifice cross-section of the first lumen lower orifice, wherein the first lumen lower orifice cross-section can have a generally ovate shape, a generally oblong shape, or a generally tear-drop shape; a second lumen upper orifice cross-section of the second lumen upper orifice, wherein the second lumen upper orifice cross-section can have a generally ovate shape, a generally oblong shape, or a generally tear-drop shape; and a second lumen lower orifice cross-section of the second lumen lower orifice, wherein the second lumen lower orifice cross-section can have a generally ovate shape, a generally oblong shape, or a generally tear-drop shape.

In some embodiments, the first lumen upper orifice cross-section can have a generally ovate shape with a first upper major axis and a first upper minor axis; the first lumen lower orifice cross-section can have a generally ovate shape with a first lower major axis and a first lower minor axis; the second lumen upper orifice cross-section can have a generally ovate shape with a second upper major axis and a second upper minor axis; and the second lumen lower orifice cross-section can have a generally ovate shape with a second lower major axis and a second lower minor axis.

In some embodiments, the conical shaped region may comprise at least a first plane of symmetry and a second plane of symmetry, wherein the first plane of symmetry is the central longitudinal plane and the second plane of symmetry is the central latitudinal plane.

In some embodiments, the multi-lumen catheter may be configured to improve fluid flow into and out from the catheter tip and to reduce undesired recirculation during hemodialysis treatment of a patient.

Further features, aspects, objects, advantages, and possible applications of the present disclosure will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present innovation will be more apparent from the following more particular description thereof, presented in conjunction with the following drawings. Like reference numbers used in the drawings may identify like components.

FIG. 2A shows a top view of an embodiment of the catheter.

FIG. 2B shows a bottom view of an embodiment of the catheter.

FIG. 4 shows a partial bottom view of an embodiment of the catheter tip.

FIG. 5 shows a partial top view of an embodiment of the catheter tip.

FIG. 6A shows a partial side view of an embodiment of the catheter tip.

FIG. 6B shows a partial side view of an embodiment of the catheter tip.

FIG. 11 shows an exemplary fluid flow that is characteristic of an embodiment of the catheter tip.

FIG. 13A shows a partial perspective view of an embodiment of the catheter tip.

FIG. 13B shows a partial perspective view of an embodiment of the catheter tip.

FIG. 14 shows a cross-section of one embodiment of the catheter body.

DETAILED DESCRIPTION

Figure 1:
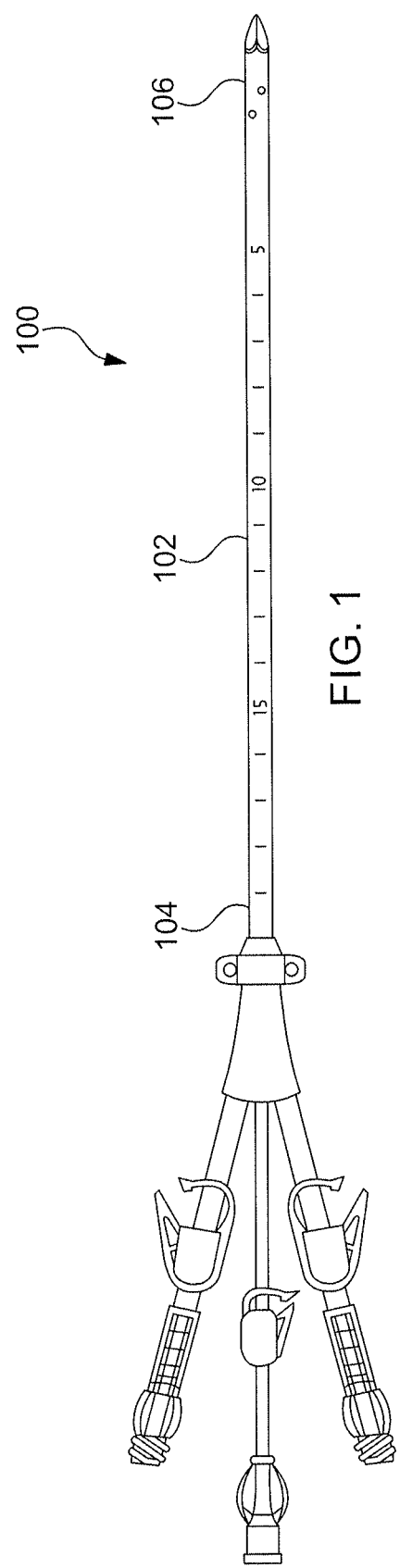
FIG. 1 shows an embodiment of the catheter in combination with a connector.
Figure 3:
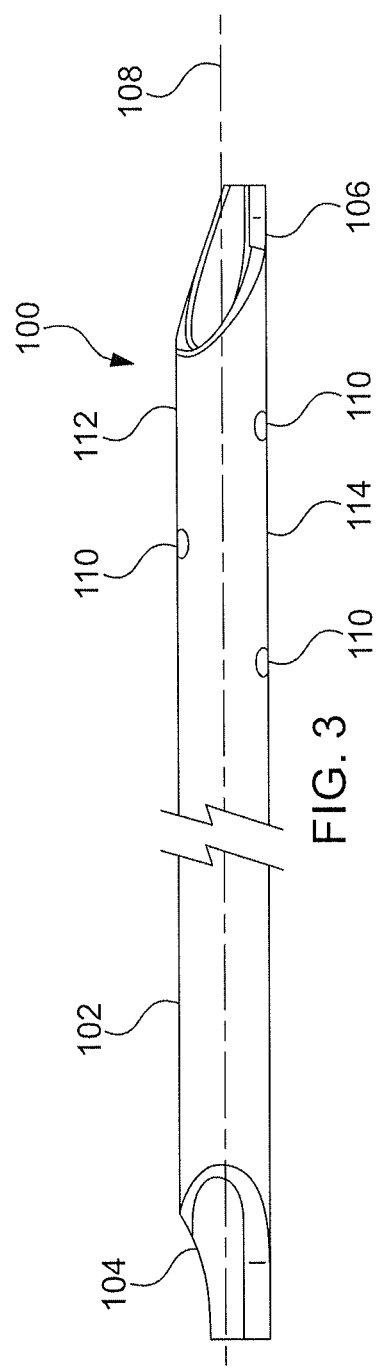
FIG. 3 shows a side view of an embodiment of the catheter.

The following description is of exemplary embodiments that are presently contemplated for carrying out the present disclosure. This description is not to be taken in a limiting sense, but is made merely for the purpose of describing the general principles and features of the present disclosure. The scope of the present disclosure is not limited by this description.

Referring to FIGS. 1-5, embodiments of the catheter 100 can include a catheter body 102 having a catheter proximal end 104 and a catheter distal end 106 with a central longitudinal axis 108 extending from the catheter proximal end 104 to the catheter distal end 106. The catheter body 102 can be a tubular member made from plastic, silicone, rubber, etc. The catheter body 102 can have a catheter top 112, a catheter bottom 114, a catheter first side 116, and a catheter second side 118. The catheter proximal end 104 can be configured to connect to a pump, reservoir, or other device for providing means to cause fluid to flow into and out from the catheter 100.

The catheter distal end 106 can be formed into a catheter tip 120. The catheter tip 120 can be configured to be inserted into a portion of a patient's body. For example, the catheter tip 120 can be tapered so as to facilitate spearheading the insertion of the catheter 100 into a patient's body, which may include insertion into a vein of the patient.

The catheter tip 120 can have at least one aperture 110 extending through the catheter top 112 or the catheter bottom 114. In at least one embodiment, the catheter 100 can have at least one aperture 110 formed in a portion thereof. For example, the catheter 100 can have an aperture 110 formed in the catheter top 112. The aperture 110 can extend into at least one of the first lumen 122a and the second lumen 122b. For instance, the catheter 100 can have a first aperture 110 formed in the catheter top 112 that extends into the first lumen 122a. The catheter 100 can have a second aperture 110 formed in the catheter top 112 that extends into the second lumen 122b. Some embodiments can include at least one aperture 110 formed in the catheter bottom 114. The aperture 110 formed in the catheter bottom 114 can extend into at least one of the first lumen 122a and the second lumen 122b. For instance, the catheter 100 can have a first aperture 110 formed in the catheter bottom 114 that extends into the first lumen 122a, a second aperture 110 formed into the catheter bottom 114 that extends into the first lumen 122a, a third aperture 110 formed in the catheter bottom 114 that extends into the second lumen 122b, and a fourth aperture 110 formed into the catheter bottom 114 that extends into the second lumen 122b.

The apertures 110 can be used to prevent the catheter tip 120 from forming a vacuum when the distal end 106 the catheter 100 makes contact with a vein, which would limit movement and operability of the catheter 100. The apertures 110 relieve any suction that would be generated if the distal end 106 of the catheter 100 makes contact with a vein. However, the apertures 110 can also improve fluid flow. Placement, size, shape, and the number of apertures 110 can be set to meet specific design criteria. It has been found that use of only two apertures 110 in the catheter top 112, wherein a first aperture 110 is formed in the catheter top 112 so as to extend into the first lumen 122a and a second aperture 110 is formed into the catheter top 112 so that it extends into the second lumen 122b, provides the most beneficial effects to the fluid flow for the purposes of reducing undesired recirculation.

The catheter body 102 can include at least one lumen 122 extending through at least a portion of the catheter body 102. The lumen 122 can be formed in the catheter body 102 so that it extends from the catheter proximal end 104 to the catheter distal end 106. In some embodiments, at least a portion of the lumen 122 can extend along the central longitudinal axis 108. For example, the catheter body 102 can have a first lumen 122a extending from the catheter proximal end 104 to the catheter distal end 106 and having a first lumen orifice 172a at the catheter distal end 106. The catheter body 102 can have a second lumen 122b extending from the catheter proximal end 104 to the catheter distal end 106 and having a second lumen orifice 172b at the catheter distal end 106. The first lumen 122a can be adjacent the second lumen 122b. In some embodiments, the first lumen 122a can be separated from the second lumen 122b by a septum 124. The septum 124 can be formed between the first lumen 122a and the second lumen 122b so as to extend along a central portion of the catheter body 102 from the catheter proximal end 104 to the catheter distal end 106.

The catheter tip 120 can include a beveled shape region 130 at the distal end 106 of the catheter 100. The beveled shape region 130 can include a bevel top edge 164 at a proximal end of the beveled shape region and adjacent the catheter top 112. The bevel top edge can be straight or curved. The beveled shape region 130 can include a chamfered edge 136 at a distal end of the catheter tip 120. Within the beveled shape region 130, the septum 124 has a septum top surface 150. Within the beveled shape region 130, the first lumen 122a can have a first lumen orifice 172a having a first lumen orifice cross-section and the second lumen 122b can have a second lumen orifice 172b having a second lumen orifice cross-section.

FIG. 6 illustrates side views of the catheter tip 120. The catheter tip 120 can include a beveled shape region 130 at the distal end 106 of the catheter 100. The beveled shape region 130 can include a chamfered edge 136 (FIG. 6A) having a thickness, $Th_1$ (FIG. 6B). For example, $Th_1$ can be within a range from 0.5 mm to 2.5 mm (e.g., 1.78 mm).

A geometric plane along the central longitudinal axis 108 and extending from the catheter first side 116 to the catheter second side 118 defines a central latitudinal plane 128 (FIGS. 6A and 6B). A geometric plane parallel to the central latitudinal plane 128 and bisecting the septum top surface 150 at the top of the lumen orifice 172 defines an upper latitudinal plane 170 (FIGS. 6A and 6B). The septum top surface 150 can be bisected by the central latitudinal plane 128 at a central latitudinal axis 158 and the septum top surface 150 can be bisected by the upper latitudinal plane 170 at an upper latitudinal axis 156 (FIG. 6B). Within the beveled shape region 130, the septum 124 can have a septum first segment 160 (FIG. 6A) that extends along the septum top surface 150 from the catheter distal end 106 for a distance $D_1$ to the central latitudinal axis 158 (FIG. 6B). The septum 124 can have a septum second segment 162 (FIG. 6A) that extends along the septum top surface 150 from the central latitudinal axis 158 for a distance $D_2$ to the upper latitudinal axis 156 (FIG. 6B). For example, $D_1$ can be within a range from 0.25 mm to 0.75 mm (e.g., 0.54 mm) and $D_2$ can be within a range from 2.5 mm to 7.5 mm (e.g., 5.11 mm).

A geometric axis perpendicular to the central latitudinal plane 128, extending from the catheter top 112 to the catheter bottom 114, and tangential to the bevel top edge 164 defines a z-axis 174 (FIG. 6B). The beveled shape region 130 can extend for a distance, $D_3$, measured parallel to the central latitudinal plane 128, from the chamfered edge 136 at the catheter distal end 106 to the z-axis 174. For example, $D_3$ can be within a range from 6.35 mm to 7.62 mm (i.e., 7.01 mm).

The catheter body has a thickness, $Th_2$, along the central longitudinal plane 126 and extending from the catheter bottom 114 to the central latitudinal plane 128 (FIG. 6B). The catheter body has a thickness, $Th_3$, along the central longitudinal plane 126 and extending from the catheter bottom 114 to the upper latitudinal plane 170 (FIG. 6B). For example, $Th_2$ can be within a range from 0.55 mm to 3.4 mm (e.g., 1.96 mm) and $Th_3$ can be within a range from 1.0 mm to 8.7 mm (e.g., 3.48 mm).

Figure 7:
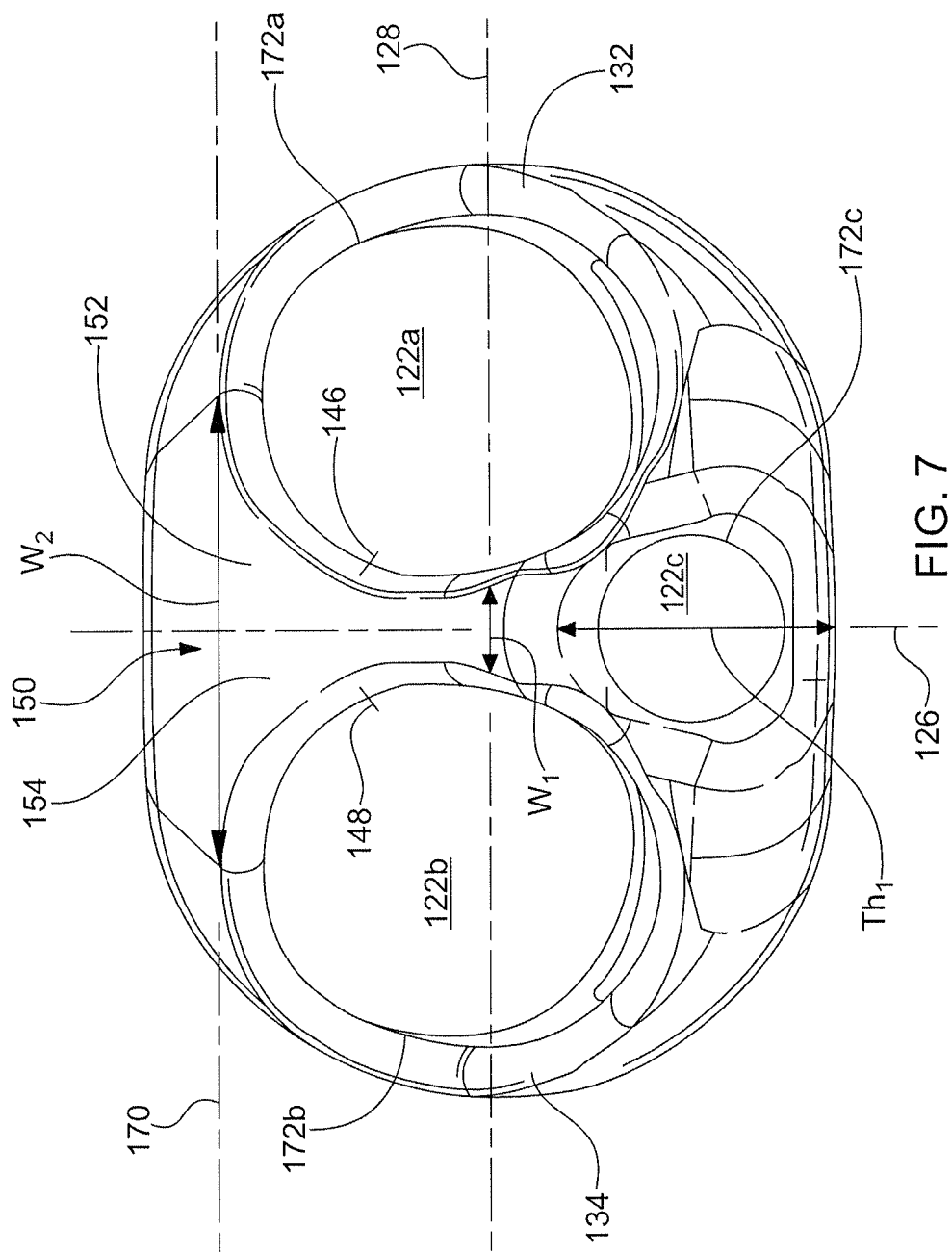
FIG. 7 shows a front view of an embodiment of the catheter tip illustrating exemplary dimensions of aspects of the catheter tip.

FIG. 7 is a front view of the beveled shape region 130 of the catheter tip 120. A geometric plane along the central longitudinal axis 108 and extending from the catheter first side 116 to the catheter second side 118 defines a central latitudinal plane 128. A geometric plane parallel to the central latitudinal plane 128 and bisecting the septum top surface 150 at the top of the first lumen 122a and the second lumen 122b defines an upper latitudinal plane 170. The septum top surface 150 can have a width, $W_1$, where the septum top surface 150 is bisected by the central latitudinal plane 128. The septum top surface 150 can have a width, $W_2$, where the septum top surface 150 is bisected by the upper latitudinal plane 170. $W_1$ can be less than $W_2$. For example, $W_1$ can be within a range from 0.25 mm to 1.5 mm (e.g., 0.51 mm) and $W_2$ can be within a range from 1.5 mm to 3.5 mm (e.g., 2.65 mm).

The beveled shape region 130 can have a first sidewall 132 forming an outer portion of the first lumen 122a and a second sidewall 134 forming an outer portion of the second lumen 122b. For example, the first lumen 122a can be formed within the catheter body 102 and share a first sidewall 132 with that of the catheter first side 116. The second lumen 122b can be formed within the catheter body 102 and share a second sidewall 134 with that of the catheter second side 118.

Septum 124 can have a septum first side 146 forming an inner portion of the first lumen 122a and a septum second side 148 forming an inner portion of the second lumen 122b. For example, the septum first side 146 can form at least part of the first lumen 122a and the septum second side 148 can form at least part of the second lumen 122b. For example, the first lumen 122a can extend along the catheter body 102 adjacent the catheter first side 116 so that the first sidewall 132 and the septum first side 146 form the first lumen 122a. The second lumen 122b can extend along the catheter body 102 adjacent the catheter second side 118 so that the second sidewall 134 and the septum second side 148 form the second lumen 122b.

At least a portion of the septum first side 146 can have an arcuate shape. For example, the portion of the septum first side 146 leading up into the septum top surface 150 can be arched. At least a portion of the septum second side 148 can have an arcuate shape. For example, the portion of the septum second side 148 leading up into the septum top surface 150 can be arched.

The septum top surface 150 can be bisected by central longitudinal plane 126. The half of the septum top surface 150 spanning from the central longitudinal plane 126 to the first lumen orifice 172a and the region of the septum first side 146 leading up into the septum top surface 150 can be referred to as the first eave 152. The half of the septum top surface 150 spanning from the central longitudinal plane 126 to the second lumen orifice 172b and the region of the septum second side 148 leading up into the septum top surface 150 can be referred to as the second eave 154. For example, the first eave 152 formed over the first lumen 122a includes a region of the septum first side 146 leading up into the septum top surface 150 and the half of the septum top surface 150 spanning from the central longitudinal plane 126 to the first lumen orifice 172a. The second eave 154 formed over the second lumen 122b includes a region of the septum second side 148 leading up into the septum top surface 150 and the half of the septum top surface 150 spanning from the central longitudinal plane 126 to the lumen second lumen orifice 172b. The first eave 152 can have a curved or arched shape that forms at least a portion of the first lumen orifice 172a and the second eave 154 can have a curved or arched shape that forms at least a portion of the second lumen orifice 172b. In some embodiments, the first eave 152 acts as a baffle to direct fluid flow out from the first lumen 122a via the first lumen orifice 172a, while restricting cross-over fluid flow to the second lumen orifice 172b, thereby reducing undesired recirculation. In some embodiments, the second eave 154 acts as a baffle to direct fluid flow out from the second lumen 122b via the second lumen orifice 172b, while restricting cross-over fluid flow to the first lumen orifice 172a, thereby reducing undesired recirculation.

The beveled shape region 130 can have a chamfered edge 136 having a thickness, $Th_1$. For example, $Th_1$ can be within a range from 0.5 mm to 2.5 mm (e.g., 1.78 mm).

In some embodiments, the catheter 100 can have a third lumen 122c having a third lumen orifice 172c at the catheter distal end 106. The third lumen 122c can extend along the catheter body 102, extending from the catheter proximal end 104 to the catheter distal end 106. The third lumen 122c can be positioned adjacent the first lumen 122a and adjacent the second lumen 122b. For example, the third lumen 122c can be positioned below the septum 124 and adjacent the catheter bottom 114. In some embodiments, the third lumen can have a generally circular shaped cross-section. In some embodiments, the third lumen 122c can be configured to facilitate insertion of a guidewire for easier manipulation of the catheter 100.

Figure 8:
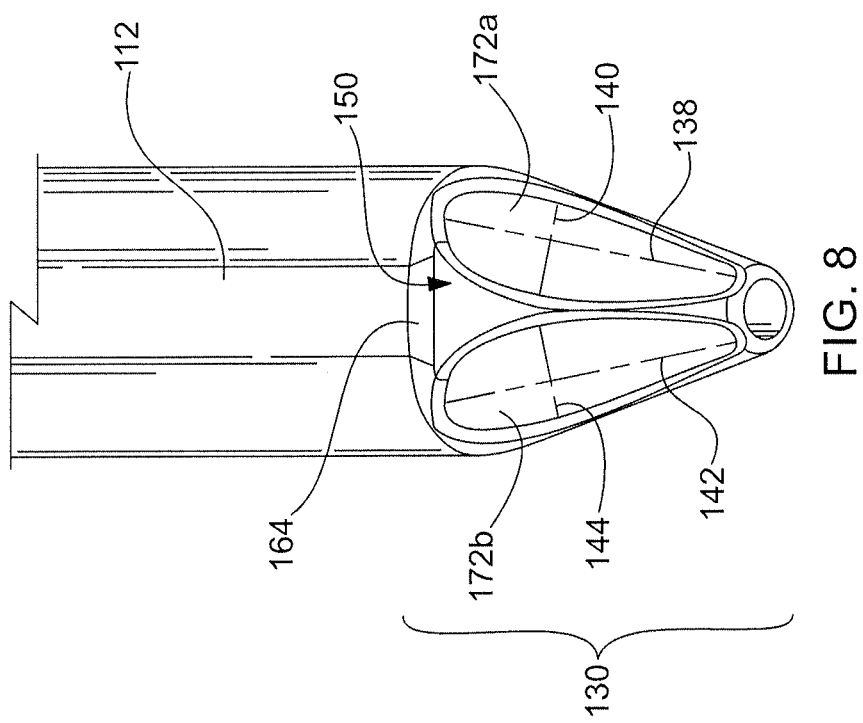
FIG. 8 shows a partial top view of an embodiment of the catheter tip illustrating exemplary dimensions of aspects of the catheter tip.

FIG. 8 illustrates a top perspective view of the catheter tip 120. Within the beveled shape region 130, the catheter top 112 can lead into the septum top surface 150. For example, within the catheter body 102, the septum 124 can be a member extending from the catheter bottom 114 to the catheter top 112, but within the beveled shape region 130, the catheter top 112 gives way to (meaning to lead into and take the shape of) the septum top surface 150. The beveled shape region 130 can have a bevel top edge 164 at a proximal end of the beveled shape region and adjacent the catheter top 112. For example, the bevel top edge can be straight. In some embodiments, the bevel top edge can be curved.

Within the beveled shape region 130, the first lumen 122a can have a first lumen orifice 172a having a first lumen orifice cross-section. The first lumen orifice cross-section can have a generally ovate shape, a generally oblong shape, or a generally tear-drop shape, etc. Within the beveled shape region 130, the second lumen 122b can have a second lumen orifice 172b having a second lumen orifice cross-section. The second lumen orifice cross-section can have a generally ovate shape, a generally oblong shape, or a generally tear-drop shape, etc. For example, the first lumen orifice cross-section can have a generally ovate shape with a first major axis 138 and a first minor axis 140. The second lumen orifice cross-section can have a generally ovate shape with a second major axis 142 and a second minor axis 144. In some embodiments, the length of the first major axis 138 equals the length of the second major axis 142 and the length of the first minor axis 140 equals the length of the second minor axis 144. For example, any one of the first major axis 138 and the second major axis 142 can be within a range from 5.0 mm to 10.0 mm (e.g., 7.06 mm) and any one of the first minor axis 140 and the second minor axis 144 can be within a range from 0.5 mm to 3.0 mm (e.g., 1.47 mm). A ratio of a first major axis 138 to a first minor axis 140 can be within a range from 3 to 5 (e.g., 4.8). A ratio of a second major axis 142 to a second minor axis 144 can be within a range from 3 to 5 (e.g., 4.8).

In some embodiments, the first major axis 138 is not an axis of symmetry. In some embodiments, the second major axis 142 is not an axis of symmetry. In some embodiments, the first minor axis 140 is not an axis of symmetry. In some embodiments, the second minor axis 144 is not an axis of symmetry.

Figure 9:
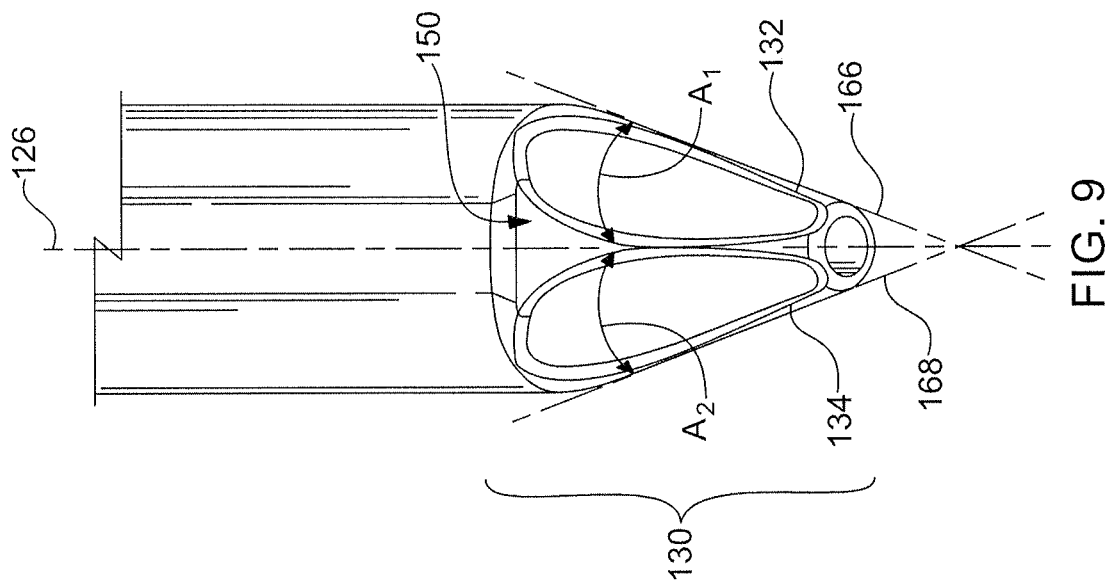
FIG. 9 shows a partial top view of an embodiment of the catheter tip illustrating exemplary dimensions of aspects of the catheter tip.

FIG. 9 illustrates a top perspective view of the catheter tip 120. The beveled shape region 130 can have a first sidewall 132 forming an outer portion of the first lumen 122a and a second sidewall 134 forming an outer portion of the second lumen 122b. A first lateral plane 166 tangential to the first sidewall 132 and normal to the central latitudinal plane 128 can be offset from the central longitudinal plane 126 by an angle $A_1$. A second lateral plane 168 tangential to the second sidewall 134 and normal to the central latitudinal plane 128 can be offset from the central longitudinal plane 126 by an angle $A_2$. For example, Angle $A_1$ can be within a range from 10 degrees to 30 degrees (e.g., 17.5 degrees) and Angle $A_2$ can be within a range from 10 degrees to 30 degrees (e.g., 17.5 degrees). It is contemplated for the angle $A_1$ to be equal to or essentially equal to the angle $A_2$. In some embodiments, $A_1$ does not equal $A_2$.

Figure 10A:
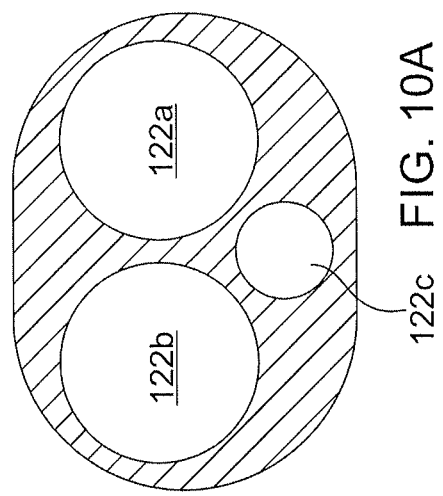
FIG. 10A shows a cross-section of one embodiment of the catheter body.
Figure 10:
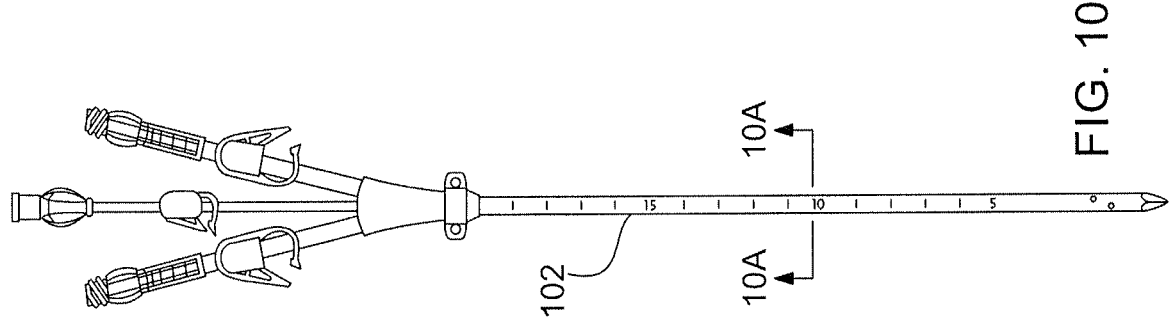
FIG. 10 shows an embodiment of the catheter in combination with a connector.

Referring to FIG. 10, in at least one embodiment, the catheter body 102 can be configured to have an oval or stadium shaped cross-section (FIG. 10A). For example, the catheter top 112 and the catheter bottom 114 can be of equal length, the catheter first side 116 and the catheter second side 118 can be of equal length, and the catheter top 112 and the catheter bottom 114 can each be longer than each of the catheter first side 116 and the catheter second side 118. The catheter body 102 where the catheter top 112 meets the catheter first side 116 can be smooth or arched, the catheter body 102 where the catheter top 112 meets the catheter second side 118 can be smooth or arched, the catheter body 102 where the catheter bottom 114 meets the catheter first side 116 can be smooth or arched, and the catheter body 102 where the catheter bottom 114 meets the catheter second side 118 can be smooth or arched.

For example, cross-section "A-A" can be stadium shaped (FIG. 10A). For instance, the catheter body 102 can have a height, $H_1$, defined along the central longitudinal plane 126 and extending from the catheter top 112 to the catheter bottom 114 that is within a range from 3.175 mm to 4.445 mm (e.g., 3.886 mm). The catheter body 102 can have a width, $W_3$, defined along the central latitudinal plane 128 and extending from the catheter first side 116 to the catheter second side 118 that is within a range from 3.81 mm to 6.35 mm (e.g., 5.36 mm).

Referring to FIG. 11, the shapes, dimensions, and ratios thereof disclosed herein are specifically designed to improve the performance of the catheter when used for hemodialysis (e.g., when fluid is being ejected from one lumen 122 and received by another lumen 122). For example, the catheter 100 can be used for hemodialysis treatment, in which the first lumen 122a is used as the suction line (withdrawing toxic blood) and the second lumen 122b is used as the return line (returning treated blood). It should be noted that the first lumen 122a can be used as the return line while the second lumen 122b is used as the suction line. The configuration of the catheter tip 120, and in particular the ramp of the septum 124 within the beveled shape region 130 and the septum top surface 150 forming the eaves 152, 154, provides improved fluid flow (an increase in the amount and rate of toxic blood being withdrawn via one lumen orifice 172 and an increase in the amount and rate of treated blood being introduced via another lumen orifice 172) with reduced undesired recirculation (i.e., a decrease in the amount and rate of treated blood being introduced via the return line that is undesirably withdrawn via the suction line). The eaves 152, 154 act as baffles to direct fluid flow out from the lumen 122 via the lumen orifice 172, while restricting cross-over fluid flow, thereby reducing undesired recirculation. For example, blood exiting the first lumen 122a via the first lumen orifice 172a is significantly restricted by the eaves 152, 154 so as to not flow into the path of the second lumen 122b and be entrained within the suction force of the second lumen 122b. This can result in a significant reduction of treated blood being withdrawn back via the second lumen orifice 172b throughout the hemodialysis treatment. This result can improve reliability and efficiency of the hemodialysis treatment. Additional improvements in fluid flow are achieved by limiting the catheter tip 120 to the angles (angle $A_1$ and angle $A_2$), the major axes and minor axes dimensions, and the ratios of the dimensions disclosed herein. In addition, embodiments of catheter 100 having a plane of mirror symmetry coplanar with central longitudinal plane 126 improve fluid flow, as well as provide for self-dilation. That is, embodiments of catheter 100 having improved fluid flow and which are capable of self-dilation can have mirror symmetry of the first lumen 122a with the second lumen 122b, mirror symmetry of the first lumen orifice 172a with the second lumen orifice 172b, and mirror symmetry of the first eave 152 with the second eave 154. In some embodiments, a third lumen 122c can be configured to facilitate insertion of a guidewire for easier manipulation of the catheter 100.

In alternative embodiments, the catheter 500 can include a catheter body 502 having a catheter proximal end 504 and a catheter distal end 506 with a central longitudinal axis 508 extending from the catheter proximal end 504 to the catheter distal end 506. The catheter body 502 can be a tubular member made from plastic, silicone, rubber, etc. The catheter body 502 can have a catheter top 512, a catheter bottom 514, a catheter first side 516, and a catheter second side 518. The catheter proximal end 504 can be configured to connect to a pump, reservoir, or other device for providing means to cause fluid to flow into and out from the catheter 500.

The catheter distal end 506 can be formed into a catheter tip 520. The catheter tip 520 can be configured to be inserted into a portion of a patient's body. For example, the catheter tip 520 can be tapered so as to facilitate spearheading the insertion of the catheter 500 into a patient's body, which may include insertion into a vein of the patient.

The catheter tip 520 can have at least one aperture 510 extending through the catheter top 512 or the catheter bottom 514. In at least one embodiment, the catheter 500 can have at least one aperture 510 formed in a portion thereof. For example, the catheter 500 can have an aperture 510 formed in the catheter top 512. The aperture 510 can extend into at least one of the first lumen 522a and the second lumen 522b. For instance, the catheter 500 can have a first aperture 510 formed in the catheter top 512 that extends into the first lumen 522a. The catheter 500 can have a second aperture 510 formed in the catheter top 512 that extends into the second lumen 522b. Some embodiments can include at least one aperture 510 formed in the catheter bottom 514. The aperture 510 formed in the catheter bottom 514 can extend into at least one of the first lumen 522a and the second lumen 522b. For instance, the catheter 500 can have a first aperture 510 formed in the catheter bottom 514 that extends into the first lumen 522a, a second aperture 510 formed into the catheter bottom 514 that extends into the first lumen, a third aperture 510 formed in the catheter bottom 514 that extends into the second lumen 522b, and a fourth aperture 510 formed into the catheter bottom 514 that extends into the second lumen 522b.

The catheter body 502 can include at least one lumen 522 extending through at least a portion of the catheter body 502. The lumen 522 can be formed in the catheter body 502 so that it extends from the catheter proximal end 504 to the catheter distal end 506. In some embodiments, at least a portion of the lumen 522 can extend along the central longitudinal axis 508. For example, the catheter body 502 can have a first lumen 522a extending from the catheter proximal end 504 to the catheter distal end 506 and having a first lumen upper orifice $572a_1$ and a first lumen lower orifice $572a_2$ at the catheter distal end 506. The catheter body 502 can have a second lumen 522b extending from the catheter proximal end 504 to the catheter distal end 506 and having a second lumen upper orifice $572b_1$ and a second lumen lower orifice $572b_2$ at the catheter distal end 506. The first lumen 522a can be adjacent the second lumen 522b. In some embodiments, the first lumen 522a can be separated from the second lumen 522b by a first septum 524. The first septum 524 can be formed between the first lumen 522a and the second lumen 522b so as to extend along a central portion of the catheter body 502 from the catheter proximal end 504 to the catheter distal end 506.

Figure 12C:
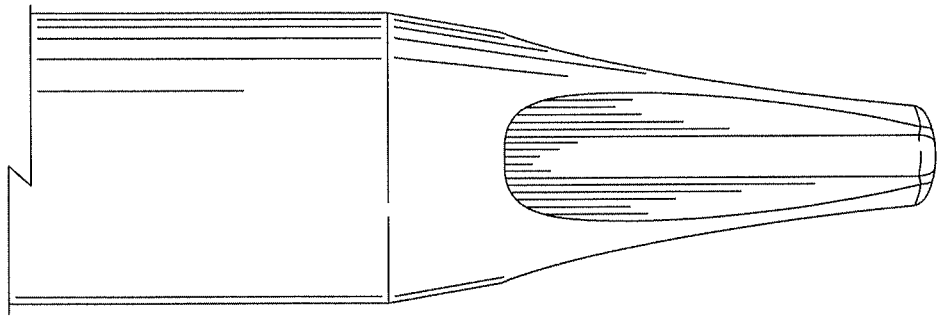
FIG. 12C shows a partial side view of an embodiment of the catheter tip.
Figure 12B:
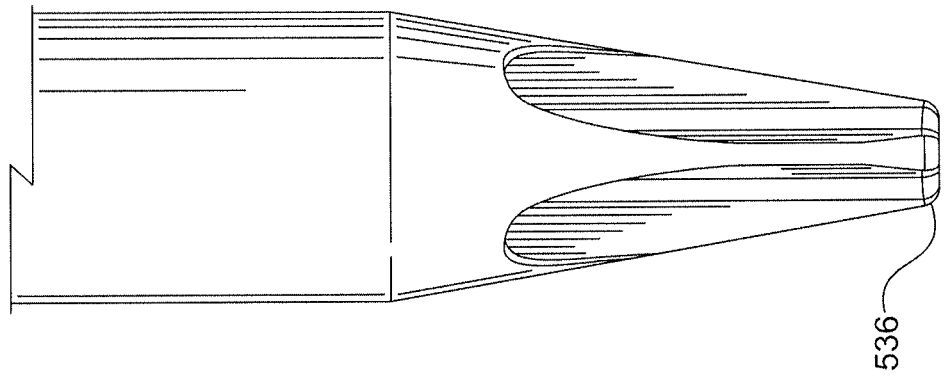
FIG. 12B shows a partial top view of an embodiment of the catheter tip.
Figure 12A:
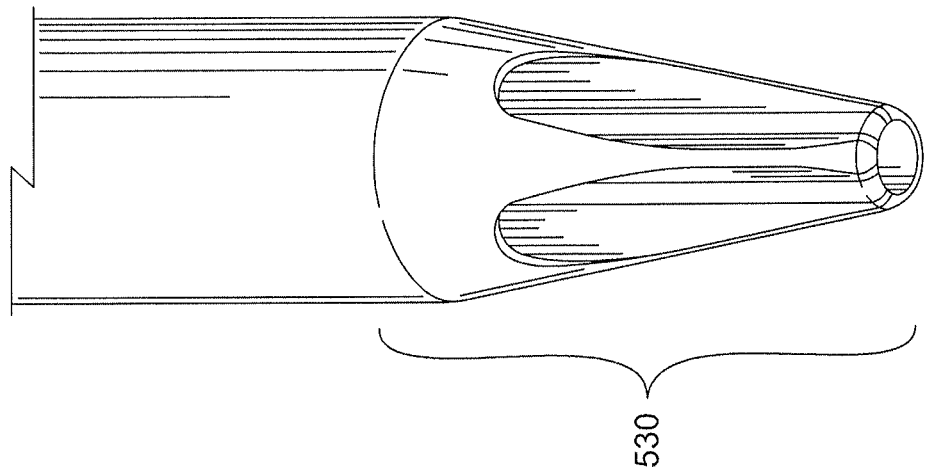
FIG. 12A shows a partial perspective view of an embodiment of the catheter tip.

FIG. 12 illustrates a perspective view, a top view, and a side view of the catheter tip 520. The catheter tip 520 can include a conical shaped region 530 at the distal end 506 of the catheter 500. The conical shaped region 530 can have a conical frustum shape having a flat distal edge 536. The flat distal edge 536 of the conical shaped region 530 can have a thickness, $Th_4$.

Figure 13C:
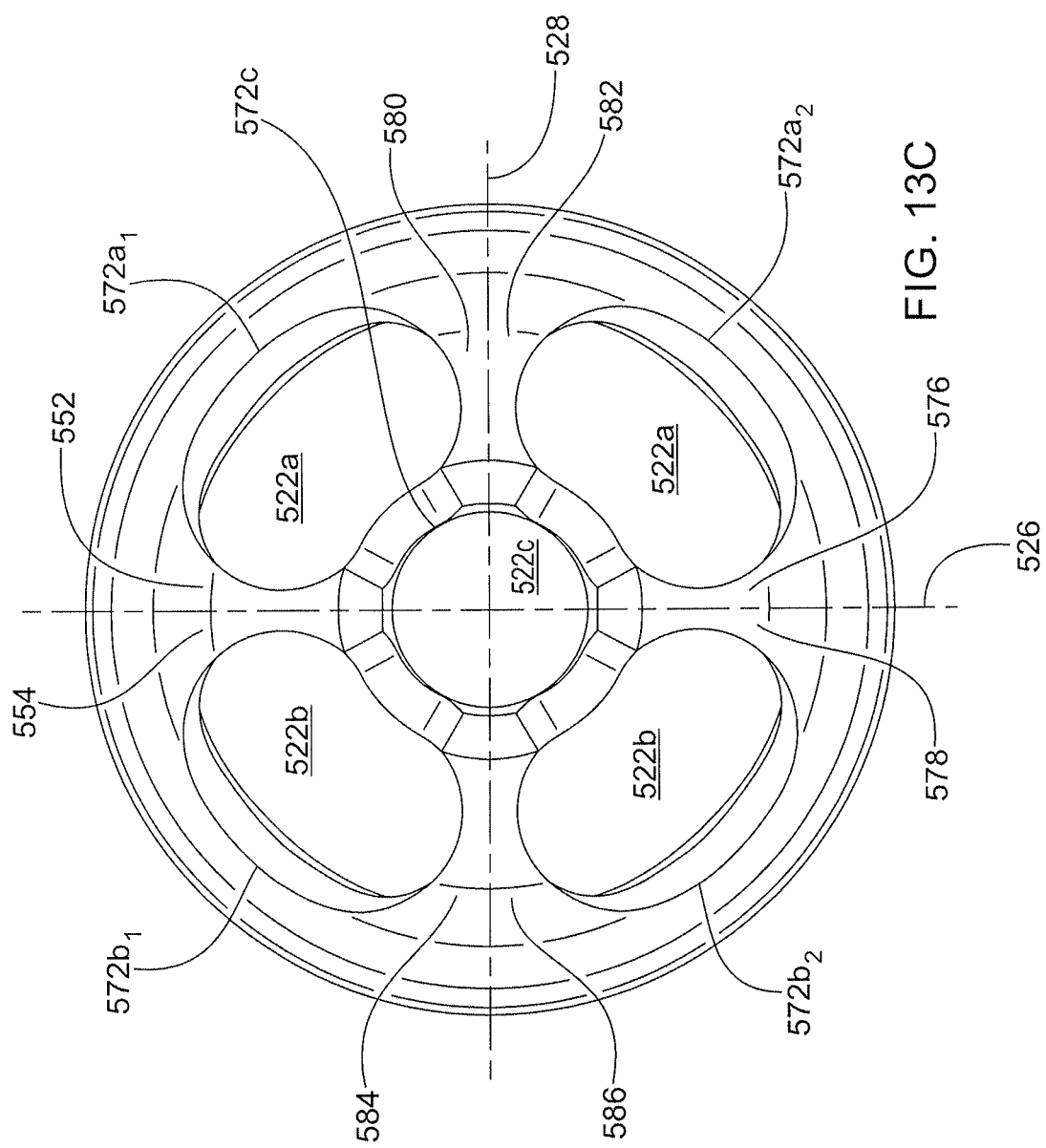
FIG. 13C shows a front view of an embodiment of the catheter tip.

FIG. 13 illustrates perspective views (FIGS. 13A and 13B) and a front view (FIG. 13C) of the conical shaped region 530 of the catheter tip 520. FIG. 13A is oriented such that the septum top surface 550a is located at the top of FIG. 13A. FIG. 13B is a perspective view that is oriented 90 degrees clockwise relative to the view shown in FIG. 13A.

First septum 524a can have a first septum first side 546a forming an inner portion of the first lumen 522a and a first septum second side 548a forming an inner portion of the second lumen 522b. For example, the first septum first side 546a can form at least part of the first lumen 522a and the first septum second side 548a can form at least part of the second lumen 522b.

Second septum 524b can have a second septum first side 546b and a second septum second side 548b. Second septum 524b can extend from a proximal end of the conical shaped region to the distal end 506 of the catheter 500. Second septum 524b can bisect at least a portion of the first lumen 522a such that the first lumen 522a has a first lumen upper orifice $572a_1$ and a first lumen lower orifice $572a_2$. Second septum 524b can bisect at least a portion of the second lumen 522b such that the second lumen 522b has a second lumen upper orifice $572b_1$ and a second lumen lower orifice $572b_2$.

Within the conical shaped region 530, the first septum 524a and the second septum 524b can have a plurality of surfaces. The first septum 524a can have a septum top surface 550a separating the first lumen upper orifice $572a_1$ from the second lumen upper orifice $572b_1$. The first septum 524a can have a septum bottom surface 550b separating the first lumen lower orifice $572a_2$ from the second lumen lower orifice $572b_2$. The second septum 524b can have a septum first lateral surface 550c separating the first lumen upper orifice $572a_1$ from the first lumen lower orifice $572a_2$. The second septum 524b can have a septum second lateral surface 550d separating the second lumen upper orifice $572b_1$ from the second lumen lower orifice $572b_2$.

At least a portion of the first septum first side 546a can have an arcuate shape. For example, the portion of the first septum first side 546a leading up into the septum top surface 550a can be arched and the portion of the first septum first side 546a leading up into the septum bottom surface 550b can be arched. At least a portion of the first septum second side 548a can have an arcuate shape. For example, the portion of the first septum second side 548a leading up into the septum top surface 550a can be arched and the portion of the first septum second side 548a leading up into the septum bottom surface 550b can be arched.

At least a portion of the second septum first side 546b can have an arcuate shape. For example, the portion of the second septum first side 546b leading up into the septum first lateral surface 550c can be arched and the portion of the second septum first side 546b leading up into the septum second lateral surface 550d can be arched. At least a portion of the second septum second side 548b can have an arcuate shape. For example, the portion of the second septum second side 548b leading up into the septum first lateral surface 550c can be arched and the portion of the second septum second side 548b leading up into the septum second lateral surface 550d can be arched.

FIG. 13C illustrates a front view of the conical shaped region 530 of the catheter tip 520. The conical shaped region can have a plurality of lumen orifices. For example, the first lumen 522a can have a first lumen upper orifice $572a_1$ and a first lumen lower orifice $572a_2$. The second lumen 522b can have a second lumen upper orifice $572b_1$ and a second lumen lower orifice $572b_2$. The third lumen 522c can have a third lumen orifice 572c.

A geometric plane along the central longitudinal axis 508 and extending from the catheter top 512 to the catheter bottom 514 defines a central longitudinal plane 526. A geometric plane along the central longitudinal axis 508, normal to the central longitudinal plane 526, and extending from the catheter first side 516 to the catheter second side 518 defines a central latitudinal plane 528.

The septum top surface 550a and the septum bottom surface 550b can be bisected by central longitudinal plane 526. The half of the septum top surface 550a spanning from the central longitudinal plane 526 to the first lumen upper orifice $572a_1$ and the region of the first septum first side 546a leading up into the septum top surface 550a can be referred to as the first eave 552. The half of the septum top surface 550a spanning from the central longitudinal plane 526 to the second lumen upper orifice $572b_1$ and the region of the first septum second side 148a leading up into the septum top surface 550a can be referred to as the second eave 554. The half of the septum bottom surface 550b spanning from the central longitudinal plane 526 to the first lumen lower orifice $572a_2$ and the region of the first septum first side 546a leading up into the septum bottom surface 550b can be referred to as the third eave 576. The half of the septum bottom surface 550b spanning from the central longitudinal plane 526 to the second lumen lower orifice $572b_2$ and the region of the first septum second side 148a leading up into the septum bottom surface 550b can be referred to as the fourth eave 578.

The septum first lateral surface 550c and the septum second lateral surface 550d can be bisected by central latitudinal plane 528. The half of the septum first lateral surface 550c spanning from the central latitudinal plane 528 to the first lumen upper orifice $572a_1$ and the region of the second septum first side 546b leading up into the septum first lateral surface 550c can be referred to as the fifth eave 580. The half of the septum first lateral surface 550c spanning from the central latitudinal plane 528 to the first lumen lower orifice $572a_2$ and the region of the second septum second side 148b leading up into the septum first lateral surface 550c can be referred to as the sixth eave 582. The half of the septum second lateral surface 550d spanning from the central latitudinal plane 528 to the second lumen upper orifice $572b_1$ and the region of the second septum first side 546b leading up into the septum second lateral surface 550d can be referred to as the seventh eave 584. The half of the septum second lateral surface 550d spanning from the central latitudinal plane 528 to the second lumen lower orifice $572b_2$ and the region of the second septum second side 148b leading up into the septum second lateral surface 550d can be referred to as the eighth eave 586.

Each of the first eave 552 and the fifth eave 580 can have a curved or arched shape that forms at least a portion of the first lumen upper orifice $572a_1$. Each of the second eave 554 and the seventh eave 584 can have a curved or arched shape that forms at least a portion of the second lumen upper orifice $572b_1$. Each of the third eave 576 and the sixth eave 582 can have a curved or arched shape that forms at least a portion of the first lumen lower orifice $572a_2$. Each of the fourth eave and the eighth eave can have a curved or arched shape that forms at least a portion of the second lumen lower orifice $572b_2$.

Each of the first eave 552 and the fifth eave 580 acts as a baffle to direct fluid flow out from the first lumen 522a via the first lumen upper orifice $572a_1$, while restricting cross-over fluid flow to the second lumen 522b, thereby reducing undesired recirculation. Each of the third eave 576 and the sixth eave 582 acts as a baffle to direct fluid flow out from the first lumen 522a via the first lumen lower orifice $572a_2$, while restricting cross-over fluid flow to the second lumen 522b, thereby reducing undesired recirculation. Each of the second eave 554 and the seventh eave 584 acts as a baffle to direct fluid flow out from the second lumen 522b via the second lumen upper orifice $572b_1$, while restricting cross-over fluid flow to the first lumen 522a, thereby reducing undesired recirculation. Each of the fourth eave 578 and the eighth eave 586 acts as a baffle to direct fluid flow out from the second lumen 522b via the second lumen lower orifice $572b_2$, while restricting cross-over fluid flow to the first lumen 522a, thereby reducing undesired recirculation.

FIG. 14 illustrates a cross-section of catheter 500. The catheter body 502 can have a catheter top 512, a catheter bottom 514, a catheter first side 516, and a catheter second side 518. The catheter body 502 can have a generally circular shaped cross-section. The catheter body 502 can have a first lumen 522a extending from the catheter proximal end 504 to the catheter distal end 506, a second lumen 522b extending from the catheter proximal end 504 to the catheter distal end 506, the first lumen 522a being adjacent the second lumen 522b, the first lumen 522a being separated from the second lumen 522b by a first septum 524a. The first septum 524a can extend along the central longitudinal plane 526 from the catheter proximal end 504 to the catheter distal end 506. The catheter body 502 can have a third lumen 522c extending from the catheter proximal end 504 to the catheter distal end 506. The third lumen 522c can be positioned adjacent the first lumen 522a and adjacent the second lumen 522b. The third lumen 522c can have a generally circular shaped cross-section. The third lumen 522c can be positioned centrally within the catheter body 502 such that the third lumen 522c bisects the first septum 524a.

Embodiments of catheter 500 disclosed herein are specifically designed to improve the performance of the catheter when used for hemodialysis (e.g., when fluid is being ejected from one lumen 522 and received by another lumen 522). For example, the catheter 500 can be used for hemodialysis treatment, in which the first lumen 522a is used as the suction line (withdrawing toxic blood) and the second lumen 522b is used as the return line (returning treated blood). It should be noted that the first lumen 522a can be used as the return line while the second lumen 522b is used as the suction line. The configuration of the catheter tip 520, and in particular the angle of the conical shaped region 530 and the septum surfaces 550a, 550b, 550c, and 550d forming the eaves 552, 554, 576, 578, 580, 582, 584, and 586, provides improved fluid flow (an increase in the amount and rate of toxic blood being withdrawn via one lumen orifice 572 and an increase in the amount and rate of treated blood being introduced via another lumen orifice 572) with reduced undesired recirculation (i.e., a decrease in the amount and rate of treated blood being introduced via the return line that is undesirably withdrawn via the suction line). The eaves 552, 554, 576, 578, 580, 582, 584, and 586 act as baffles to direct fluid flow out from the lumen 522 via the lumen orifices 572, while restricting cross-over fluid flow, thereby reducing undesired recirculation. For example, blood exiting the first lumen 522a via the first lumen upper orifices 572a is significantly restricted by the eaves 552, 576, 580, and 582 so as to not flow into the path of the second lumen 522b and be entrained within the suction force of the second lumen 522b. This can result in a significant reduction of treated blood being withdrawn back via the second lumen orifices 572b throughout the hemodialysis treatment. This result can improve reliability and efficiency of the hemodialysis treatment. In addition, embodiments of catheter 500 having a plane of mirror symmetry coplanar with the central longitudinal plane 526 and a plane of symmetry coplanar with the central latitudinal plane 528 improve fluid flow, as well as provide for self-dilation.

In some embodiments, a third lumen 522c can be configured to facilitate insertion of a guidewire for easier manipulation of the catheter 500. The third lumen 522c can extend from the catheter proximal end 504 to the catheter distal end 506 and have a third lumen orifice 572c at the catheter distal end 506. The third lumen 522c can be positioned adjacent the first lumen 522a and adjacent the second lumen 522b. The third lumen 522c can have a generally circular shaped cross-section. The third lumen 522c can be positioned centrally within the catheter body 502 such that the third lumen 522c bisects the first septum 524a and bisects the second septum 524b.

Example 1—Recirculation Analysis

Percent lumen-to-lumen recirculation was determined for an exemplary embodiment of the present disclosure shown in FIGS. 1-12, referred to as "13.5F Trio-CT" and for a traditional catheter referred to as "15.5F T-3." Two catheter lengths were tested for each of the 13.5F Trio-CT and the 15.5F T-3 catheters. A total of 30 catheters were tested as follows:
10×13.5F Trio-CT 15 cm catheter,
10×13.5F Trio-CT 30 cm catheter,
5×15.5F T-3 15 cm catheter, and
5×15.5F T-3 32 cm catheter.

Both normal and reverse flow re-circulation values were determined under a simulated use condition using saline. A two-head rotary pump was used with a flow rate of 2.5 L/min. For each of the 10 (traditional) 15.5F T-3 catheters, a single replicate experiment was conducted for each of the normal and reverse flow conditions. For each of the 20 13.5F Trio-CT catheters of the present disclosure, three replicate experiments were conducted for each of the normal and reverse flow conditions. For each condition and replicate, conductivity was measured in mili-Siemen (mS) for the water reservoir, the saline (venous) sample, and the collected (arterial) sample.

Percent recirculation was calculated using Formula 1 and averaged for replicate catheters and replicate experiments.

% Recirculation=[(Collected Fluid mS−Water Reservoir mS)/(Saline mS)]×100%  Formula 1:

Averaged % Recirculation results are shown below in Table 1.

TABLE 1

| | % Recirculation | | | | | | | |
|---|---|---|---|---|---|---|---|---|
| | 13.5 F Trio-CT | | | | 15.5 F T-3 | | | |
| | 15 cm | | 30 cm | | 15 cm | | 32 cm | |
| | Normal Flow | Reverse Flow | Normal Flow | Reverse Flow | Normal Flow | Reverse Flow | Normal Flow | Reverse Flow |
| Average | 0.42 | 0.65 | 1.44 | 1.99 | 0.00 | 7.78 | 0.00 | 7.72 |
| Max. | 2.33 | 3.16 | 4.00 | 4.64 | 0.00 | 8.39 | 0.00 | 10.46 |

Results from recirculation testing show that % recirculation is low for the traditional catheters (15.5F T-3 15 cm and 32 cm catheters) under normal flow conditions, but that % recirculation increases significantly under reverse flow for the traditional catheters. Unexpectedly, the catheters of the present disclosure (13.5F Trio-CT 15 cm and 30 cm catheters) show low % recirculation under both normal and reverse flow conditions.

It should be understood that modifications to the embodiments disclosed herein can be made to meet a particular set of design criteria. For instance, the number of or configuration of catheters 100 and 500, lumen 122 and 522, septa 124 and 524, apertures 110 and 510, and/or other components or features may be used to meet a particular objective.

It will be apparent to those skilled in the art that numerous modifications and variations of the described examples and embodiments are possible in light of the above teachings of the disclosure. The disclosed examples and embodiments are presented for purposes of illustration only. Other alternative embodiments may include some or all of the features of the various embodiments disclosed herein. Therefore, it is the intent to cover all such modifications and alternative embodiments as may come within the true scope of this disclosure, which is to be given the full breadth thereof. Additionally, the disclosure of a range of values is a disclosure of every numerical value within that range, including the end points.

Therefore, while certain exemplary embodiments of apparatuses and methods of making and using the same have been discussed and illustrated herein, it is to be distinctly understood that the disclosure is not limited thereto but may be otherwise variously embodied and practiced within the scope of the following claims.

What is claimed:

1. A low recirculation multi-lumen catheter, comprising:
   an elongated catheter body comprising a catheter top, a catheter bottom, a catheter first side, and a catheter second side;
   a proximal end;
   a distal end having a catheter tip;
   a first lumen extending from the catheter proximal end to the catheter distal end and a second lumen extending from the catheter proximal end to the catheter distal end, wherein the first lumen is substantially parallel to the second lumen;
   a septum comprising a septum first side adjacent the first lumen and a septum second side adjacent the second lumen, wherein the septum separates the first lumen from the second lumen;
   a central longitudinal axis extending from the catheter proximal end to the catheter distal end;
   a central longitudinal plane comprising the central longitudinal axis and extending from the catheter top to the catheter bottom; and
   a beveled shape region, having bilateral symmetry along the central longitudinal plane, comprising a first lumen orifice, a second lumen orifice, at least a portion of the septum first side, at least a portion of the septum second side, and a septum top surface; wherein
      the first lumen orifices and second lumen orifices locate entirely within the beveled shape region,
      the first lumen orifices and second lumen orifices having generally ovate shape;
      at least a portion of the septum first side and at least a portion of the septum top surface form a first eave over the first lumen; and
      at least a portion of the septum second side and at least a portion of the septum top surface form a second eave over the second lumen;
      the first eave and the second eave extends to at least half of the septum top surface;
      the first eave is configured to act as a baffle, when the first lumen is used to introduce fluid, to direct fluid flow out from the first lumen via the first lumen orifice, while restricting cross-over fluid flow to the second lumen;
      the second eave is configured to act as a baffle, when the second lumen is used to introduce fluid, to direct fluid flow out from the second lumen via the second lumen orifice, while restricting cross-over fluid flow to the first lumen; and
      the first eave comprises a region of the septum first side leading up into the septum top surface and a half of the septum top surface spanning from the central longitudinal plane to the first lumen orifice, the first eave have an arched shape that forms at least a portion of the first lumen orifice; and
      the second eave comprises a region of the septum second side leading up into the septum top surface and a half of the septum top surface spanning from the central longitudinal plane to the second lumen orifice, the second eave have an arched shape that forms at least a portion of the second lumen orifice.

2. The multi-lumen catheter of claim 1, comprising:
   a central latitudinal plane comprising the central longitudinal axis and extending from the catheter first side to the catheter second side;
   an upper latitudinal plane parallel to the central latitudinal plane and bisecting the septum top surface at the top of the first lumen orifice and at the top of the second lumen orifice;
   a central latitudinal axis extending along the central latitudinal plane and bisecting the septum top surface; and
   an upper latitudinal axis extending along the upper latitudinal plane and bisecting the septum top surface.

3. The multi-lumen catheter of claim 1, wherein
   the first lumen can be a dedicated suction line or a dedicated return line; and
   the second lumen can be a dedicated suction line or a dedicated return line.

4. The multi-lumen catheter of claim 2, wherein the catheter body comprises
   a generally oval or stadium shaped cross-section;
   a height, $H_1$, measured along the central longitudinal axis and extending from the catheter bottom to the catheter top; and
   a width, $W_3$, measured along the central latitudinal axis and extending from the catheter first side to the catheter second side;
   wherein $H_1$ is less than $W_3$.

5. The multi-lumen catheter of claim 2, wherein the septum comprises
   a width, $W_1$, measured along the central latitudinal axis and extending from the septum first side to the septum second side; and
   a width, $W_2$, measured along the upper latitudinal axis and extending from the septum first side to the septum second side,
   wherein $W_1$ is less than $W_2$.

6. The multi-lumen catheter of claim 2, wherein the beveled shape region comprises a chamfered edge at the distal end of the catheter, the chamfered edge having a thickness, $Th_1$, measured along the central longitudinal plane.

7. The multi-lumen catheter of claim 1, wherein the beveled shape region comprises a bevel top edge at a proximal end of the beveled shape region and adjacent the catheter top, wherein the bevel top edge can be straight or curved.

8. The multi-lumen catheter of claim 2, wherein the septum comprises:
   a septum first segment extending along the septum top surface from the catheter distal end for a distance, $D_1$, to the central latitudinal axis; and a septum second segment extending along the septum top surface from the central latitudinal axis for a distance, $D_2$, to the upper latitudinal axis.

9. The multi-lumen catheter of claim 6, wherein the beveled shape region extends for a distance, $D_3$, measured parallel to the central latitudinal plane, from the chamfered edge at the catheter distal end to a z-axis;
   wherein the z-axis is perpendicular to the central latitudinal plane, tangential to the bevel top edge, and extends from the catheter top to the catheter bottom.

10. The multi-lumen catheter of claim 2, wherein the catheter body has a thickness, $Th_2$, and a thickness $Th_3$, wherein
   $Th_2$ is measured along the central longitudinal plane and extends from the catheter bottom to the central latitudinal plane; and
   $Th_3$ is measured along the central longitudinal plane and extends from the catheter bottom to the upper latitudinal plane.

11. The multi-lumen catheter of claim 1, wherein the catheter body comprises at least one aperture extending through the catheter top and into at least one of the first lumen and the second lumen.

12. The multi-lumen catheter of claim 1, wherein the catheter body comprises at least one aperture extending through the catheter bottom and into at least one of the first lumen and the second lumen.

13. The multi-lumen catheter of claim 1, further comprising a third lumen adjacent the first lumen and adjacent the second lumen.

14. The multi-lumen catheter of claim 2, wherein the beveled shape region comprises
   a first sidewall forming an outer portion of the first lumen; and
   a second sidewall forming an outer portion of the second lumen;
   wherein a first lateral plane tangential to the first sidewall and normal to the central latitudinal plane is offset from the central longitudinal plane by an angle, $A_1$; and
   a second lateral plane tangential to the second sidewall and normal to the central latitudinal plane is offset from the central longitudinal plane by an angle, $A_2$.

15. The multi-lumen catheter of claim 1, wherein the beveled shape region comprises
   a first lumen orifice cross-section of the first lumen orifice, wherein the first lumen orifice cross-section can have a generally ovate shape, a generally oblong shape, or a generally tear-drop shape; and
   a second lumen orifice cross-section of the second lumen orifice, wherein the second lumen orifice cross-section can have a generally ovate shape, a generally oblong shape, or a generally tear-drop shape.

16. The multi-lumen catheter of claim 15, wherein the first lumen orifice cross-section has a generally ovate shape with a first major axis and a first minor axis and the second lumen orifice cross-section has a generally ovate shape with a second major axis and a second minor axis.

17. The multi-lumen catheter of claim 2, wherein the beveled shape region comprises at least one plane of symmetry, wherein the plane of symmetry is the central longitudinal plane.

18. The multi-lumen catheter of claim 1, wherein the catheter is configured to improve fluid flow into and out from the catheter tip and to reduce undesired recirculation during hemodialysis treatment of a patient.

* * * * *